(12) United States Patent
Hayden et al.

(10) Patent No.: US 11,919,786 B2
(45) Date of Patent: Mar. 5, 2024

(54) BIAS ENHANCED ELECTROLYTIC PHOTOCATALYSIS (BEEP) CLEANING SYSTEM

(71) Applicant: Waterdrape, LLC, Paradise Valley, AZ (US)

(72) Inventors: John B. Hayden, Paradise Valley, AZ (US); Sapanbir S. Thind, Victoria (CA)

(73) Assignee: Waterdrape, LLC, Paradise Valley, AZ (US)

( * ) Notice: Subject to any disclaimer, the term of this patent is extended or adjusted under 35 U.S.C. 154(b) by 0 days.

(21) Appl. No.: 18/045,491

(22) Filed: Oct. 11, 2022

(65) Prior Publication Data

US 2023/0113314 A1  Apr. 13, 2023

Related U.S. Application Data

(60) Provisional application No. 63/373,502, filed on Aug. 25, 2022, provisional application No. 63/255,221, filed on Oct. 13, 2021.

(51) Int. Cl.
| | |
|---|---|
| *C02F 1/467* | (2023.01) |
| *C02F 1/32* | (2023.01) |
| *C02F 1/461* | (2023.01) |
| *C02F 101/30* | (2006.01) |
| *C02F 101/36* | (2006.01) |

(Continued)

(52) U.S. Cl.
CPC ............ *C02F 1/4672* (2013.01); *C02F 1/325* (2013.01); *C02F 1/46109* (2013.01); *C02F 2001/46142* (2013.01); *C02F 2001/46157* (2013.01); *C02F 2001/46171* (2013.01); *C02F 2101/308* (2013.01); *C02F 2101/36* (2013.01); *C02F 2103/08* (2013.01); *C02F 2103/42* (2013.01); *C02F 2201/3222* (2013.01); *C02F 2201/3223* (2013.01); *C02F 2201/3225* (2013.01); *C02F 2303/04* (2013.01)

(58) Field of Classification Search
None
See application file for complete search history.

(56) References Cited

U.S. PATENT DOCUMENTS

| | | | |
|---|---|---|---|
| 7,241,950 | B2 | 7/2007 | Fan et al. |
| 7,296,785 | B2 | 11/2007 | Hayden |
| 7,344,124 | B2 | 3/2008 | Hayden |

(Continued)

FOREIGN PATENT DOCUMENTS

| | | |
|---|---|---|
| CN | 208927931 U | 6/2019 |
| WO | 2010132993 A1 | 11/2010 |

OTHER PUBLICATIONS

Loeb et al.; "The Technology Horizon for Photocatalytic Water Treatment: Sunrise or Sunset?" Environ. Sci. Technol.; 2019; vol. 53; pp. 2937-2947.

(Continued)

*Primary Examiner* — Richard C Gurtowski
(74) *Attorney, Agent, or Firm* — BakerHostetler

(57) ABSTRACT

Methods and systems for the purification of an aqueous solution comprising a photocatalyst employed as an anode and a cathode in communication with an electrolyte to achieve a current flow wherein a charge is applied between the cathode and the photocatalytic excited anode a corresponding increase in electron-hole pairs occurs.

6 Claims, 18 Drawing Sheets

(51) Int. Cl.
 *C02F 103/08* (2006.01)
 *C02F 103/42* (2006.01)

(56) References Cited

U.S. PATENT DOCUMENTS

| | | |
|---|---|---|
| 7,500,656 B2 | 3/2009 | Hayden |
| 9,868,129 B2 | 1/2018 | Hayden |
| 10,143,956 B2 | 12/2018 | Hayden |
| 10,329,180 B2 | 6/2019 | Hayden |
| 2009/0074611 A1 | 3/2009 | Monzyk et al. |
| 2012/0279872 A1 | 11/2012 | Chen et al. |
| 2013/0029016 A1* | 1/2013 | Gottenbos ............ C25B 1/55 |
| | | 99/323.1 |
| 2013/0140244 A1 | 6/2013 | Barry et al. |
| 2015/0064064 A1 | 3/2015 | Kim et al. |
| 2015/0076045 A1 | 3/2015 | Lee et al. |

OTHER PUBLICATIONS

Notification of Transmittal of the International Search Report and the Written Opinion of the International Searching Authority, or the Declaration dated Dec. 29, 2022.

* cited by examiner

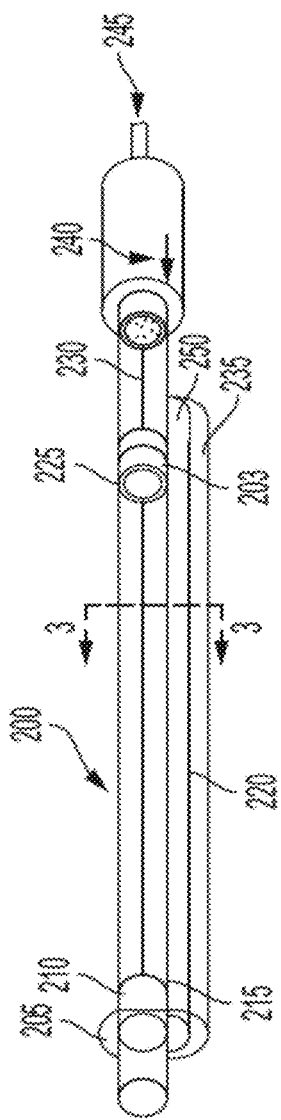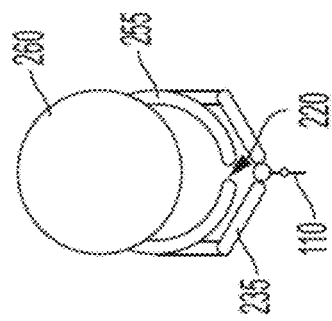
FIG. 7A
FIG. 7B

BIAS ENHANCED ELECTROLYTIC PHOTOCATALYSIS (BEEP) CLEANING SYSTEM

CROSS REFERENCE TO RELATED APPLICATIONS

This application claims the benefit of U.S. Provisional App. Ser. No. 63/255,221, filed Oct. 13, 2021, and U.S. Provisional App. Ser. No. 63/373,502, filed Aug. 25, 2022, the entire contents of which are incorporated by reference herein.

FIELD OF THE DISCLOSURE

The present disclosure relates generally to air and/or water cleaning systems. In particular, air and water cleaning systems comprising photocatalysis occurring on an anode.

BACKGROUND OF THE DISCLOSURE

Water covers seventy percent of the Earth's surface. Waterbodies are under intense pressure from commerce, transportation, and resource exploitation. Over-fishing is also of considerable concern. Efforts to create sustainable aquatic production tend to create additional environmental impact. Marine pollution is particularly relevant since forty percent of the world's population resides within one hundred kilometers of an oceanic coast.

Outflows from wastewater and run-off contain compounds that promote algal blooms that reduce available oxygen to shore-life while other pollutants impact the entire marine environment(s) (both fresh and marine). Coastal impacts include changes to barrier islands flora resulting in significant loss to infrastructure and habitations. Additionally, a portion of this local population relies on potable water that is generated through saline reverse osmosis of the very seawater they impact.

Reducing biofouling as well as the need to remove or destroy pollutants, volatile organic chemicals, pathogens, petroleum, and other compounds from surface, waste and industrial discharge into lakes and seawater without impacting the marine biome is of vital concern. An efficient and economical method of pollution reduction is needed.

Current technologies for water and air purification mainly rely on filtration. Filtration primarily removes suspended materials and is generally limited to reducing chemical compounds through sequestration via carbon filtration. Filtration systems further require monitoring and replacement. Once captured, these compounds remain within the filters presenting a disposal requirement and can become a potential secondary pollution source.

Chemical disinfection using oxygenating compounds is effective at sanitizing water, however, these chemicals remain in the drinking water and create additional chemical byproducts which are known to be cancer-causing. These chemicals are a significant source of volatile organic compounds (VOC) in drinking water. These residual effects make dumping chemicals in the oceans a poor solution.

Other methods of removing pathogens from air and water include irradiation with ultraviolet (UV) light. Unfortunately, not all pathogens are susceptible to ultraviolet UV light. For example, UV-C light is effective against DNA viruses but less so for RNA viruses. In fact, many pathogens are resilient to UV light due to normal environmental exposure. Efforts to reduce marine biofouling using UV-C light has had limited success and is inappropriate for the many challenges the environment faces.

Moreover, perfluoroalkyl substances (PFAS), also referred to as "forever chemicals" due to their lack of degradability, have recently emerged as an area of growing concern and regulation. Currently, there are few ways of controlling PFAS, and most of these methods are energy intensive and/or rely on harsh processing.

Water containing ionic compounds and impurities generally result in a decrease in the efficiency of photocatalysis by adsorption, scavenging, or other interferences. Photocatalytic water treatment is discussed in "The Technology Horizon for Photocatalytic Water Treatment: Sunrise or Sunset?" Loeb et al., Environ. Sci. Technol. 2019, 53, 2937-2947, hereby incorporated by reference in its entirety. While heterogeneous photocatalysis-based advanced oxidation processes (AOP) have been used in the abatement of organic pollutants, they have never gained a significant adoption due to limitations in efficiency and design. To further expand on photocatalytic adoption beyond recent advancements referenced within this application, an additional means of decreasing electron-hole pair re-combination was necessary.

Methods and systems for combined photocatalytic and electrochemical wastewater remediation are disclosed in WO 2010/132993 (U.S. Patent Application Publication 2012/0279872), hereby incorporated by reference in its entirety.

Current photocatalytic water treatment systems may be limited by the formation of adsorbed material on the photocatalysts; the recombination of electron-hole pairs which results in decrease in generated reactive oxidizing species; and low photo-conversion efficiency.

To be energy efficient, electrolysis requires an ionic solution that must conduct between two poles without generating excess heat. At high potentials due to water splitting, the production of hydrogen from an aqueous solution during electrolysis can cause potentially explosive conditions. Furthermore, generating excess chlorine compounds from a saline solution through electrolysis while useful in some applications is not always desirous. Accordingly, there remains a need for new water purification technologies.

SUMMARY OF THE DISCLOSURE

The foregoing needs are met, by a system, comprising a light source configured to emit light at a wavelength; a photocatalytic anode radially disposed around the light source configured to be illuminated by the light source; a cathode radially disposed around the photocatalytic anode; a power source electronically connected to the photocatalyst and the cathode and configured to apply a positive charge to the photocatalyst and a negative charge to the cathode; and an ionic aqueous liquid in between the photocatalyst and the cathode, where the ionic aqueous liquid creates electrical communication between the photocatalyst and cathode, where the light source illuminates the photocatalyst to excite electrons and generate electron-hole pairs in the photocatalyst.

One general aspect includes a system, configured to emit light at a wavelength, a cathode radially disposed around the light source that allows the light transmission to a photocatalyst radially disposed around the cathode and configured to be illuminated by the light source, a power source electronically connected to the photocatalyst and the cathode and configured to apply a positive charge to the photocatalyst and a negative charge to the cathode, and an ionic aqueous liquid in between the photocatalyst and the cathode, wherein the ionic aqueous liquid creates electrical communication between the photocatalyst and cathode, wherein the light source illuminates the photocatalyst to excite electrons to generate electron-hole pairs in the photocatalyst.

An additional aspect includes configuring a natural light source to pass through a cathode that has a plurality of perforations or woven strands; arranging a photocatalyst anode parallel to the cathode and configured to be illuminated by the natural light source; providing a power source electronically connected to the photocatalyst and the cathode, configured to apply a positive charge to the photocatalyst and a negative charge to the cathode; and providing an ionic aqueous liquid in between the photocatalyst and the cathode, where the ionic aqueous liquid creates electrical communication between the photocatalyst and cathode, where the light source illuminates the photocatalyst to excite electron-hole pairs in the photocatalyst. The cathode can also be below the anode such that the photocatalyst anode is directly exposed to the natural light.

Embodiments of the disclosure can relate to methods and systems which use bias to enhance photocatalysis.

An aspect of the disclosure includes a method of cleaning pollutants from a medium, by configuring a photocatalytic anode to be in electrical communication with a cathode, generating a bias between the photocatalytic anode and the cathode configuring a light source to emit light at a wavelength at a photocatalytic anode, emitting light from the light source, and cleaning the medium by placing the medium in communication with the photocatalytic anode.

There has thus been outlined, rather broadly, certain embodiments of the disclosure in order that the detailed description thereof and herein may be better understood, and in order that the present contribution to the art may be better appreciated. There are, of course, additional embodiments of the disclosure that will be described below and which will form the subject matter of the claims appended hereto.

In this respect, before explaining at least one embodiment of the disclosure in detail, it is to be understood that the disclosure is not limited in its application to the details of construction and to the arrangements of the components outlined in the following description or illustrated in the drawings. The disclosure is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

BRIEF DESCRIPTION OF THE DRAWINGS

FIG. 7A is a diagrammatic representation of a piston assembly according to an embodiment of the disclosure.

FIG. 7B is a cross-sectional view taken along 3-3 in FIG. 7A.

DETAILED DESCRIPTION

Figure 1:
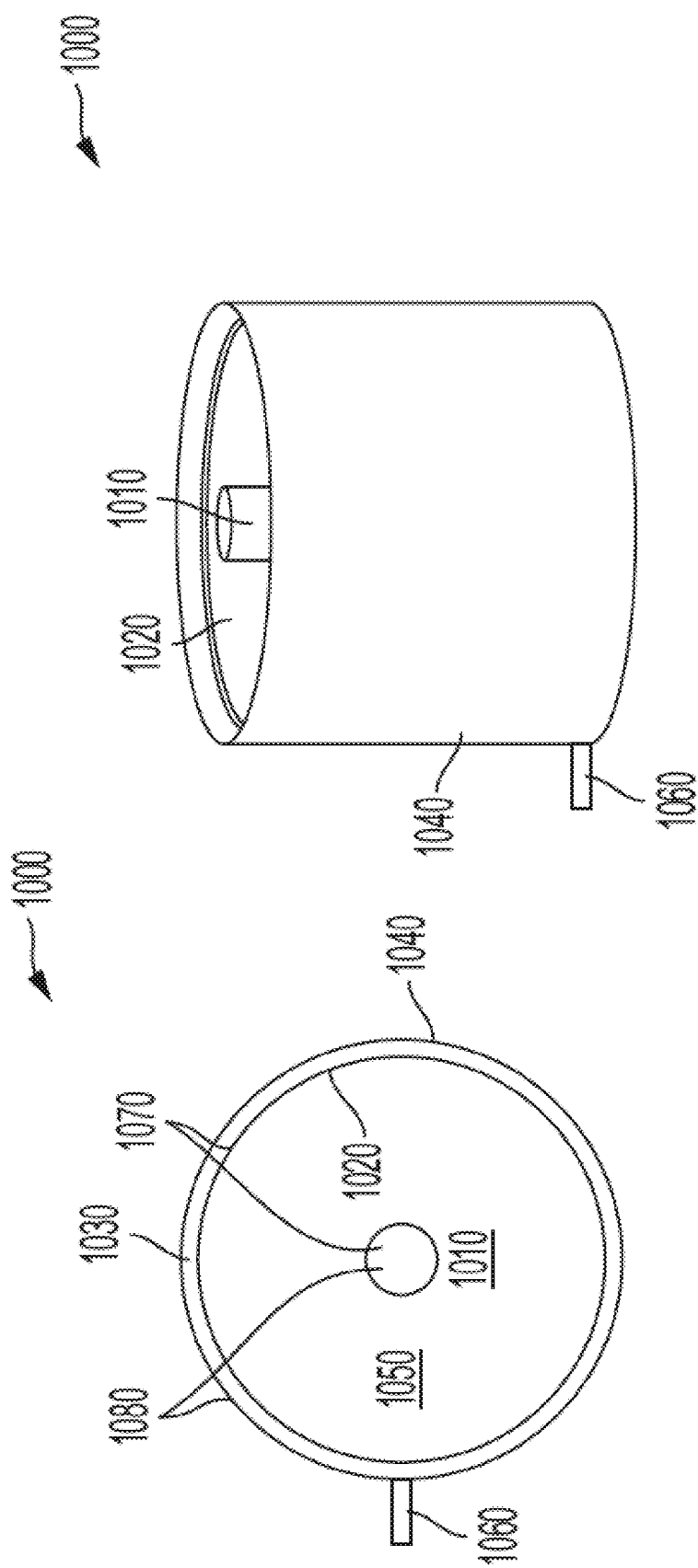
FIG. 1 is a diagram of a flow-through electrolytic photocatalytic system according to aspects of the disclosure.

Before certain embodiments are described in greater detail, it is to be understood that this disclosure is not limited to certain embodiments described, as such may, of course, vary. It is also to be understood that the terminology used herein is for the purpose of describing certain embodiments only, and is not intended to be limiting, since the scope of the present disclosure will be limited only by the appended claims.

Described herein are several definitions. Such definitions are meant to encompass grammatical equivalents.

The use of "or" means "and/or" unless stated otherwise. Furthermore, the use of the terms "comprising," "having," "including," as well as other forms, such as "includes" and "included," are intended to be inclusive and mean that there may be additional elements other than the listed elements.

As used herein, the term "about" when referring to a measurable value such as an amount, a temporal duration, and the like, is meant to encompass variations. Such variations, however, are dependent on the specific component referred to and the context as understood by a person of ordinary skill in the art. Unless specifically indicated otherwise, values described are intended to encompass "about" the value.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, representative illustrative methods, and materials are now described.

Each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible. In addition, various embodiments may be combined mutatis mutandis to form a single embodiment.

The disclosure will now be further described with reference to the drawing figures, in which like reference numerals refer to like parts throughout.

Embodiments of the disclosure can be practiced without any component not specifically mentioned in this disclosure. Specifically, while not literally referenced, a component not listed herein can be excluded based on the understanding of a person of ordinary skill in the art as such component may change or not provide the desired functionality of the disclosure herein.

Embodiments described herein may comprise, consist essentially of, or consist of the elements therein.

Embodiments of the disclosure provide a photocatalytic component with a potential bias that are useful for cleaning both saltwater and freshwater. In some embodiments, the cleaning can be done without a change in the pH of the water.

In general, embodiments of the disclosure provide, the combination of a wavelength-specific and efficient UVA LED (light-emitting diode) light source, photocatalytic materials having nano-porous holes integral to the photocatalytic material thereby avoiding kinetic and caustic degradation and providing electrolytic transfer of the electrons from the bulk to the photocatalyst surface resulting in a decrease of electron hole-pair recombination and enhancement in the photocatalytic efficiency. Embodiments of the disclosure work with thin-film water technology thereby increasing light transmission and residency to the photocatalyst. Additional oxygenation may be employed with a wet scrubber or by communication with an airstream to yield improved production of reactive oxygen species (ROS).

Embodiments of the disclosure also relate to a method for enhancing the photocatalytic activity of a photocatalyst by applying a potential bias where a constant current or voltage is applied. In this system, an electrochemical cell is established that comprises an anode electrode and a cathode electrode. In this electrochemical cell, the photocatalyst is the anode and another metal acts as a cathode. This cathode can be constructed from any stable material such as high-quality stainless steel, titanium metal, and/or metal-coated substrate. The established electrochemical cell can be a closed cell where conducting electrolyte always remains at its position or an electrochemical cell is constructed where a solution can freely enter and leave the space between the anode and the cathode.

The voltage or current is not limited and can vary based on the particular application. For example, certain applications utilize a high voltage or current and other applications utilize a low voltage or current. Embodiments which might utilize a high voltage or current can be systems designed to clean pools, and embodiments which might utilize low voltage or current can be aquariums. The proper voltage or current may vary depending on certain factors. For example, voltages will be impacted by ionic concentration, proximity of the electrodes, surface area, etc.

In general, certain approaches employ electrochemically enhanced photocatalysis for water, air, pharmaceuticals, wastewater treatment, and/or the like. This technology generates highly oxidizing hydroxyl radicals and ROSs from the aqueous fluid within the nano-porous photocatalyst allowing this secondary fluid to interact with and oxidize the contaminants of the aqueous fluid, comprising the steps of: (1) fabricating and employing nanostructured materials as a photocatalyst ($TiO_2$, $WO_3$, $C_3N_4$, etc.); (2) exciting the photocatalyst with specific wavelength irradiation; (3) scrubbing air with a violent water sprayer; (4) flowing a thin film of this aqueous solution containing the contaminants along the photocatalyst surface; (5) enhancing the photocatalyst's activity by applying a constant potential bias or current between the photocatalyst (anode) and another metal electrode (cathode). When the photocatalyst is irradiated with a suitable light source, direct interband electron transition takes place where electrons jump from the valence band to the conduction band resulting in the creation of electron-hole pairs. Without wishing to be bound by theory, embodiments of the disclosure provide a potential bias that is applied on the photocatalyst and another electrode, due to which the electrons give the generated holes additional time to react.

FIG. 1 shows a diagram of a flow-through embodiment having supplemental oxygenation from exposure to an airstream according to aspects of the disclosure.

Aspects described in relation to FIG. 1 and/or illustrated in FIG. 1 may be utilized in any other embodiments herein. In particular, FIG. 1 illustrates a top view of an embodiment of a system 1000 on the left side and a perspective view of the system 1000 on the right of the Figure. In this regard, FIG. 1 is of an embodiment of the system 1000 that utilizes the ionic content of a water source to provide electrolytic communication between the cathode and the photocatalytic anode. After the water passes through the electrolytic chamber, the water may be disseminated over the photocatalytic surfaces. In this embodiment, the water operates in an overflow method to maintain a path for the current to flow to both sides of the photocatalytic anode of the system 1000.

The system 1000 may include and/or may utilize an electrolytic fluid 1030, an inlet 1060, a cathode 1040, a photocatalytic anode 1020, a light source 1010, and/or the like. The electrolytic fluid 1030 enters at the inlet 1060 and floods a space between the cathode 1040 and the photocatalytic anode 1020, overflowing and coating the inner surface of the photocatalytic anode 1020. Light from the light source 1010 excites the inner surface of the photocatalytic anode 1020. A negative charge is provided to the cathode 1040 via a negative pole 1080, making it a cathode that transfers a charge through the electrolytic fluid 1030 to the photocatalytic anode 1020 which is connected to the positive pole 1070, thereby completing the circuit. The atmosphere 1050 between the light source 1010 and the photocatalytic anode 1020 allows communion of the electrolytic fluid 1030 and the atmosphere 1050 until the electrolytic fluid 1030 exits the system under gravity flow.

Figure 2:
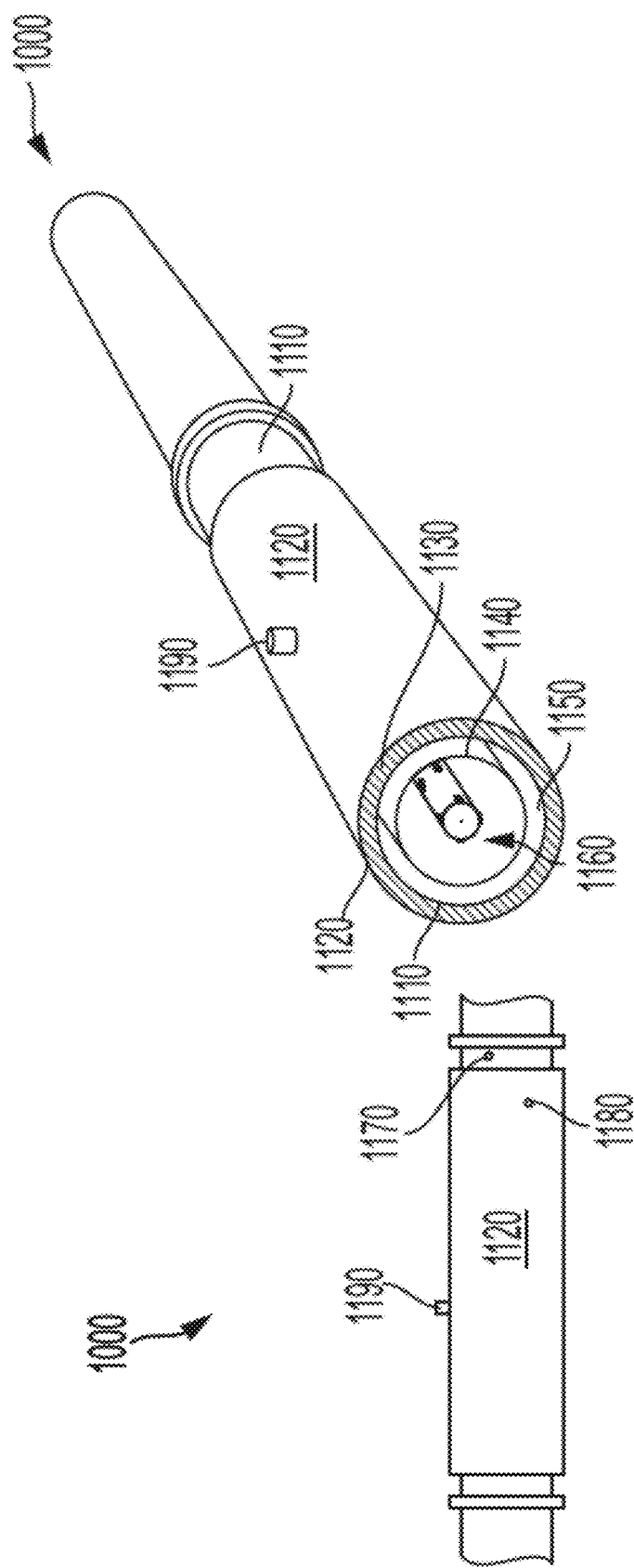
FIG. 2 shows a diagram of a closed electrolyte system according to aspects of the disclosure.

FIG. 2 is a diagram of a resident electrolytic photocatalytic system according to aspects of the disclosure.

Aspects described in relation to FIG. 2 and/or illustrated in FIG. 2 may be utilized in any other embodiments herein. In particular, FIG. 2 illustrates a side view of an embodiment of the system 1000 on the left side and a perspective view of the system 1000 on the right of the Figure. In this regard, a second embodiment of the system 1000 is provided in FIG. 2 where an electrolyte is housed between a cathode and a photocatalytic anode. The interior portions of the photocatalytic anode have holes at a nano level to form a nano-porous surface, allowing the formation of hydroxyl radicals and reactive oxygen species that interact with the water and pollutants. Current flowing from the cathode to the anode increases the likelihood of electron-hole pair formation on the semiconducting photocatalytic anode. This supplements the demand for additional oxygenation allowing a sealed system inline with a pressurized supply line.

In the second embodiment of the system 1000 provided in FIG. 2, a resident electrolyte 1130 is placed between a photocatalytic anode 1110 and an external cathode 1120 with an optional electrolyte recharging port 1190 shown. A negative pole 1180 supplies a charge to the cathode and the light source 1160, while a positive pole 1170 completes the circuit through the electrolyte 1130 and provides power to the light source 1160. Treated fluid 1150 can flow adjacent to the photocatalyst at pressurized speed, while optional a light transmissive tube, e.g. quartz glass 1140 protects the light source 1160 from exposure to the fluid. This embodiment of the system 1000 may be configured and/or may apply a method that utilizes electron transfer to the bulk of the anode material to enhance photocatalytic efficiency.

Figure 3:
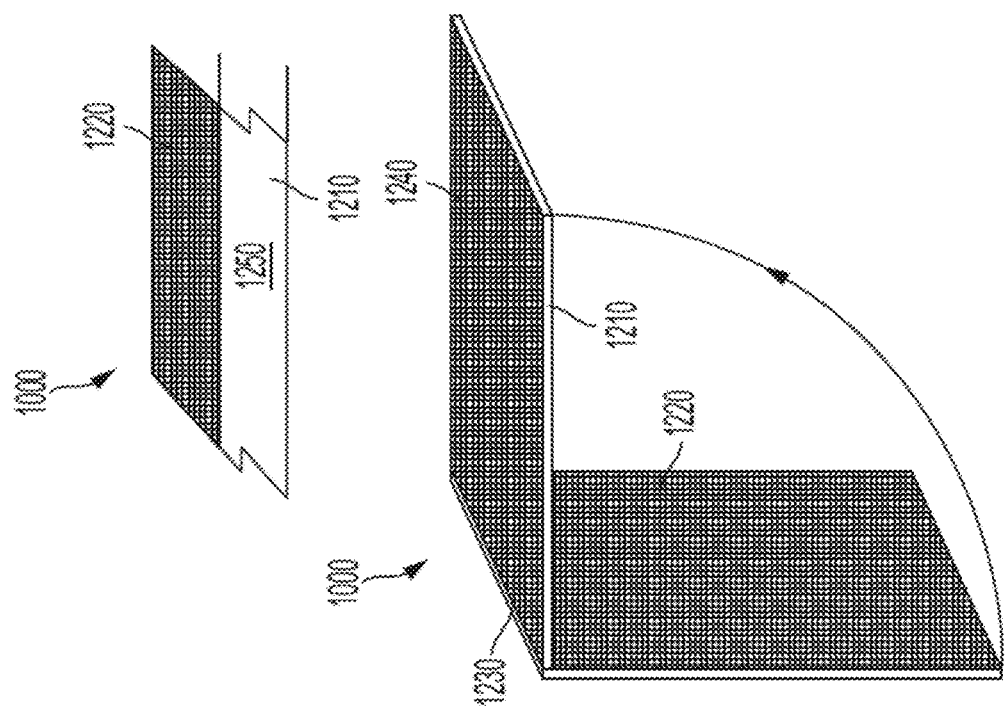
FIG. 3 is a linear representation according to aspects of the disclosure.
Figure 3:
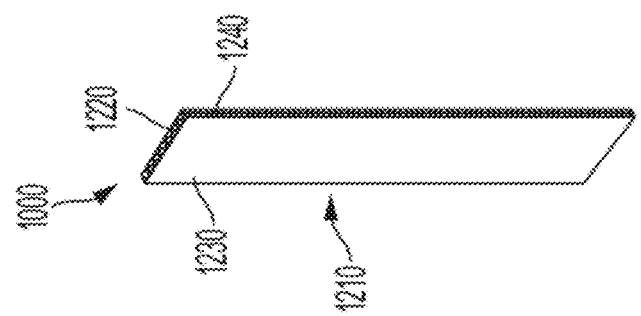

FIG. 3 is a linear representation according to aspects of the disclosure.

Aspects described in relation to FIG. 3 and/or illustrated in FIG. 3 may be utilized in any other embodiments herein. In particular, FIG. 3 illustrates three different perspective views of an embodiment of the system 1000. In particular, FIG. 3 provides an embodiment of the system 1000 employing a technique and/or configuration wherein a cathode allows light to penetrate through the electrolytic fluid to the photocatalytic anode. This version of the system 1000 can be used in a vertical or horizontal installation. The photocatalysis of this embodiment of the system 1000 can rely on natural sunlight or a light source configured to either be the sole source or a supplemental source of excitation.

The photocatalytic anode 1210, 1230 and the natural light permeable (e.g., perforated) cathode 1220, 1240 of the system 1000 are kept in contact via submersion, horizontal, vertical or inclined dissemination of an electrolytic fluid 1250 between these two materials. A positive bias is applied to the photocatalytic anode 1210, 1230 and a negative bias is connected to the natural light permeable cathode 1220, 1240.

Figure 4:
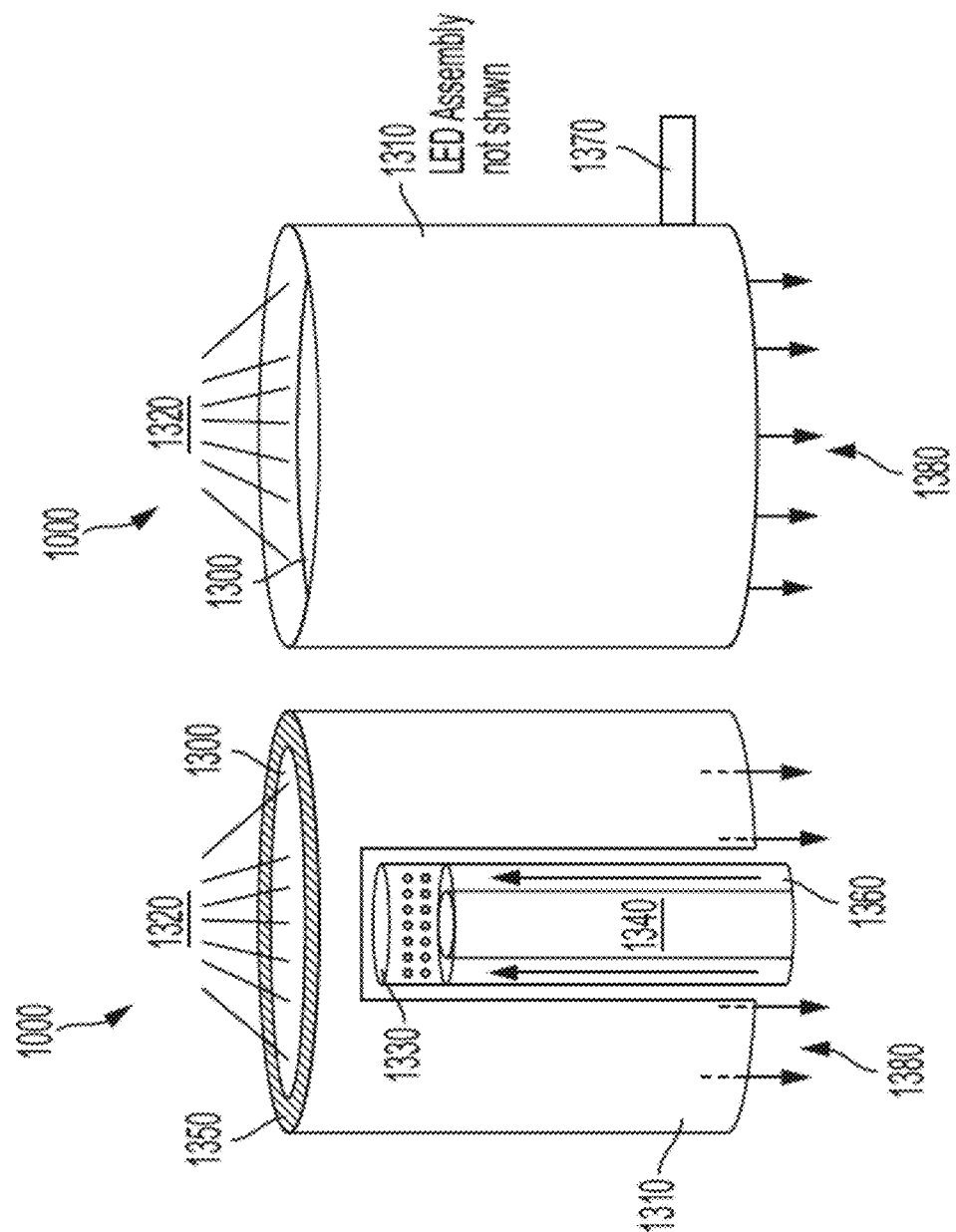
FIG. 4 shows two embodiments of the disclosure of air cleaning according to aspects of the disclosure.

FIG. 4 shows embodiments of the disclosure utilizing wet-scrubbing according to aspects of the disclosure.

Aspects described in relation to FIG. 4 and/or illustrated in FIG. 4 may be utilized in any other embodiments herein. In particular, FIG. 4 illustrates a partially transparent perspective side view of an embodiment of the system 1000 on the left side and a perspective side view of the system 1000 on the right of the Figure. FIG. 4 shows embodiments of the system 1000 of the disclosure utilizing wet-scrubbing. In FIG. 4, a means of air cleaning is disclosed for implementation with the system 1000, where air is mixed with a fluid which then flows across the photocatalytic anode. This is represented in both a resident method and a flow through method implemented by the system 1000. Moreover, 1000 may be configured for implementation of these methods. By mixing air with the fluid, oxygenation occurs as well as capturing particulate matter within the fluid.

A photocatalytic anode 1300 and a cathode 1310 are shown in this implementation of the system 1000. Ambient air or air under velocity from an air conveyor 1320 cause particulates and gases to come in contact with the fluid present. This can be either through a wet scrubber spray 1330 via pressure through inlet 1360 or via an overflow system 1370. A light source 1340 is provided to excite the photocatalyst on the photocatalytic anode 1300. Air and the treated fluid exit the system at a system output 1380. The electrolyte 1350 can be resident and not mix with the treated fluid, or the electrolytic fluid has an ionic compound enters at the overflow system 1370 and exits at the system output 1380, e.g., as an overflow.

Figure 5:
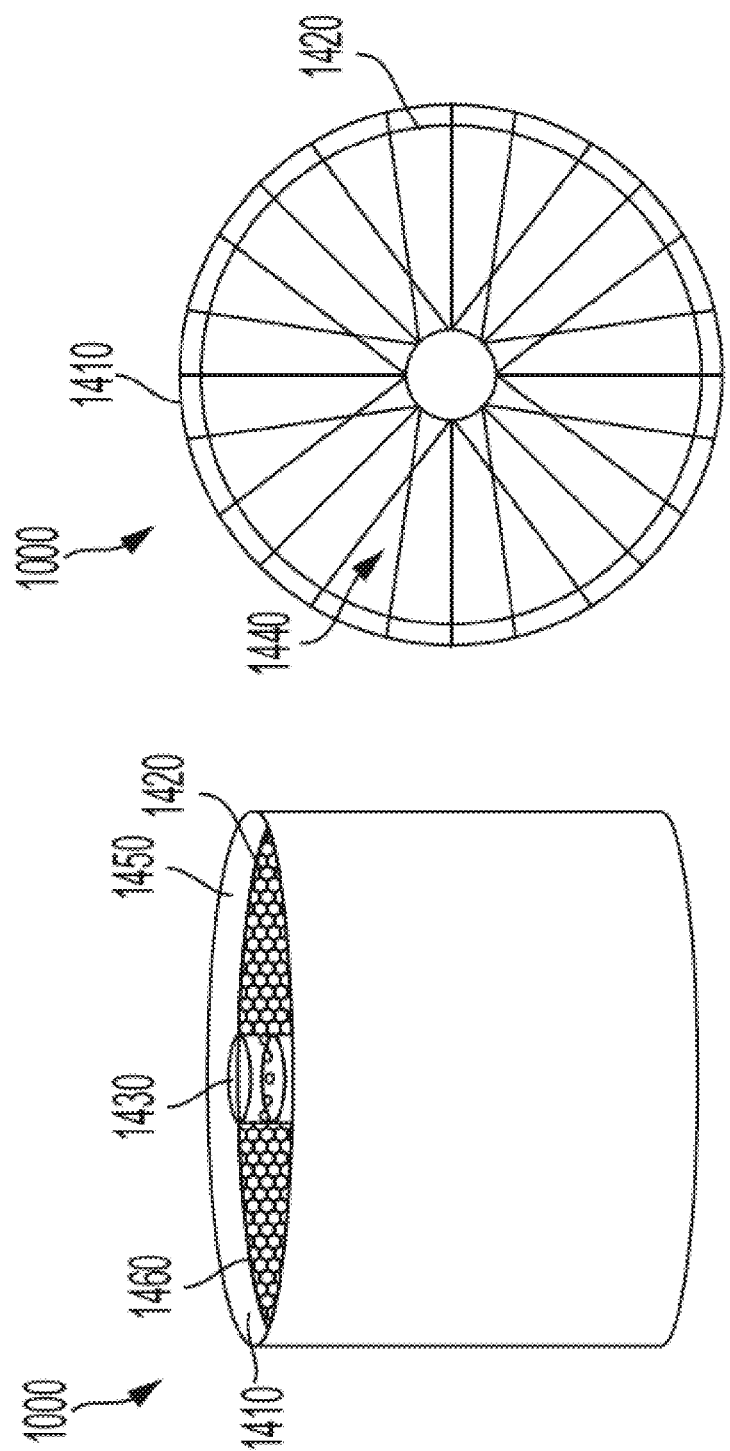
FIG. 5 is a diagram of a system according to an embodiment of the disclosure.

FIG. 5. provides another variation of air scrubbing.

Aspects described in relation to FIG. 5 and/or illustrated in FIG. 5 may be utilized in any other embodiments herein. In particular, FIG. 5 illustrates a perspective side view of an embodiment of the system 1000 on the left and a top view of the system 1000 on the right of the Figure. In this regard, FIG. 5 discloses an embodiment of the system 1000 that includes a means to allow air, fluid and light 1440 to conduct through a perforated cathode shield onto a photocatalytic anode using wet scrubbing.

In the FIG. 5 embodiment of the system 1000, the cathode 1420 allows passage of a portion of the light emitted from the light source 1430 to excite the photocatalytic anode 1410. A means to flood the photocatalytic anode 1410 while movement of this fluid maintains an electrolytic circuit by a positive pole 1450 connected to the anode and a negative pole 1460 connected to the cathode 1420.

Advanced oxidation processes (AOP) via semiconductor photocatalysis for water treatment has been the subject of research over the past several decades. Conventional AOPs employ precursor chemical oxidants, such as $O_3$ and $H_2O_2$, in combination or with an input of energy (e.g., UV irradiation), to produce reactive oxygen species (ROS) for the oxidative destruction of contaminants in water.

In photocatalytic oxidation, a precursor oxidant is turned into a ROS by a catalyst with the input of energy, usually UV light. When the photocatalyst is irradiated with UV light, electrons jump from the valence band to the conduction band resulting in the creation of electron-hole pairs. The electron-hole pairs interact with the water and dissolved oxygen molecules generating hydroxyl radicals and reactive oxygen species (ROS). The ROS/hydroxyl radicals oxidize organic and biological pollutants near the photocatalyst surface due to the ROS's highly reactive nature. In general, ROS formed include superoxide anion radicals, singlet oxygen, hydroxyl radicals, and peroxides from the aqueous solutions. Treated water may retain some residual oxidants that persist longer than hydroxyl radicals. These persistent oxidizing compounds reduce surface colonies/debris and maintain water quality while large scale organisms like fish flourish in these oxygenated waters.

Two parameters that can improve the efficiency of photocatalysis are (1) the reduction in the electron-hole pair recombination rate due to the applied potential between the two electrodes and (2) less adsorption and interference by the ionic impurities on the photocatalyst surface.

Applicable photocatalysts include: titanium oxides, zinc oxides, and other known photocatalysts. Of this group, $TiO_2$ has been investigated as a semiconductor photocatalyst for the treatment of inorganic and organic pollutants due to its band gap, chemical inertness, high efficiency, non-toxicity, and low cost.

$TiO_2$ may be one of the best materials for the degradation of hazardous pollutants due to its strong oxidizing power, high photocatalytic activity, chemical and biological stability, relatively low cost, nontoxicity, and long-term photostability. $TiO_2$ with different morphologies such as nanosphere, nanotube, nanorod, nanofiber, and nanowire can be used. In the present disclosure, the synthesis of different morphology on solid supports offers a useful application for the development and fabrication of photocatalytic reactors.

In an embodiment, the $TiO_2$ catalyst is a nanomaterial grown directly from titanium. This photocatalyst is synthesized $TiO_2$ nano-particles that are converted to a crystalline material which is an integral part of a titanium structure by annealing. Without being bound to theory, the nano-porous surface is irradiated with UVA light which creates electron-hole pairs on the surface of the $TiO_2$, these electron-hole pairs can generate $OH^{\bullet}$ radicals and additional ROS from the proximate water. The ROS then attack and destroy pollutants. The nano-porous structure of the nanomaterial surface enhances the total surface area, thereby increasing the photocatalytic effect, where the redox reaction occurs. Electrolysis can be employed to further enhance the photocatalytic activity by increasing electrons at the surface from the bulk of the material. As used herein, bias enhancement of electrolytic photocatalysis is referred to as BEEP. However, other mechanisms may also contribute to removal of pollutants.

Anodization of Titanium to Synthesize Titanium Dioxide Nanomaterials

The highly ordered $TiO_2$ nanomaterials can be grown using the anodization method. In this process, Ti was initially cleaned in acetone for 15 min, after which it was etched in boiling 18% UCl for 10 min. Electrochemical anodization can be performed at a voltage between 40-60 V in a one-compartment two-electrode cell containing an electrolytic solution. This electrolytic solution can be Dimethylsulfoxide (DMSO)+2% HF or ethylene glycol+0.3 wt % $NH_4F$+2 wt % $H_2O$. After the anodization is performed for a certain period of time, the titanium is rinsed in water followed by the annealing al 450° C. for 3 h to obtain the anatase crystal structure. A light source that produces photons having the appropriate wavelength should generate electron-hole pairs in the catalyst. Traditional light sources include sunlight or mercury lamps, however, in certain aspects the light sources are LEDs. These LEDs can generate light tuned to the range required for photocatalysis. By tuning the light, efficiency may be improved as energy is not wasted generating light which does not produce electron-hole pairs.

Specific embodiments of the system 1000 of the disclosure relate to methods and systems for enhancing the photocatalytic activity of a photocatalyst by applying a potential bias. In certain embodiments, the potential bias utilizes a constant current or voltage.

Methods of applying the potential bias include forming an electrochemical cell comprising two electrodes, an anode, and a cathode. In such an electrochemical cell, the photocatalyst is the anode and a second metal acts as a cathode. This cathode can be constructed from any stable material such as stainless steel, titanium metal, metal-coated substrate, or any conducting material which can withstand environmental conditions and operate as a cathode. In certain embodiments, the cathode is stainless steel. The established electrochemical cell can be a closed cell where the conducting electrolyte always remains at its position or an electrochemical cell is constructed where a solution can freely enter and leave the space between the anode and the cathode.

A common electrolyte that can be employed are sodium chlorine ions which are found in seawater. When the electrolyte is an aqueous solution, higher voltages may cause hydrogen production, which can require venting for safety reasons. Heat generation causes evaporation as well as water lost through electrolysis requires water volume augmentation. By adjusting the potential bias between the electrodes, hydrogen production from the aqueous solution can be reduced/eliminated as well as control of chlorine production. Non-aqueous electrolytes are known and can be employed to generate the required conductivity between the anode and cathode. The electrolyte is not limited to a specific medium, voltage or amperage.

Embodiments which employ aspects of present disclosure are discussed in U.S. Pat. Nos. 7,296,785; 7,344,124; 7,500,656; 9,868,129; 10,143,956; and 10,329,180 all incorporated by reference herein in their entireties. Certain embodiments of the system 1000 can employ integrated UV LED technology and thin water films on a nanomaterial-based photocatalytic surface. Activity may be increased by concentrating light to the specific range that yields a peak photocatalytic response. Thin flow of water can increase time for the photons to interact with the photocatalyst and proximity of the water. Water scrubbing may ensure an adequate supply of oxygenation to the water which resulted in higher production of ROS. Water scrubbing may not only clean water, but by mixing the water vigorously with an airstream create a methodology to purify ambient air from volatile organic chemicals, aerosols, and other particulates. Once captured these organics are mineralized to carbon dioxide, oxygen, and water.

Figure 6:
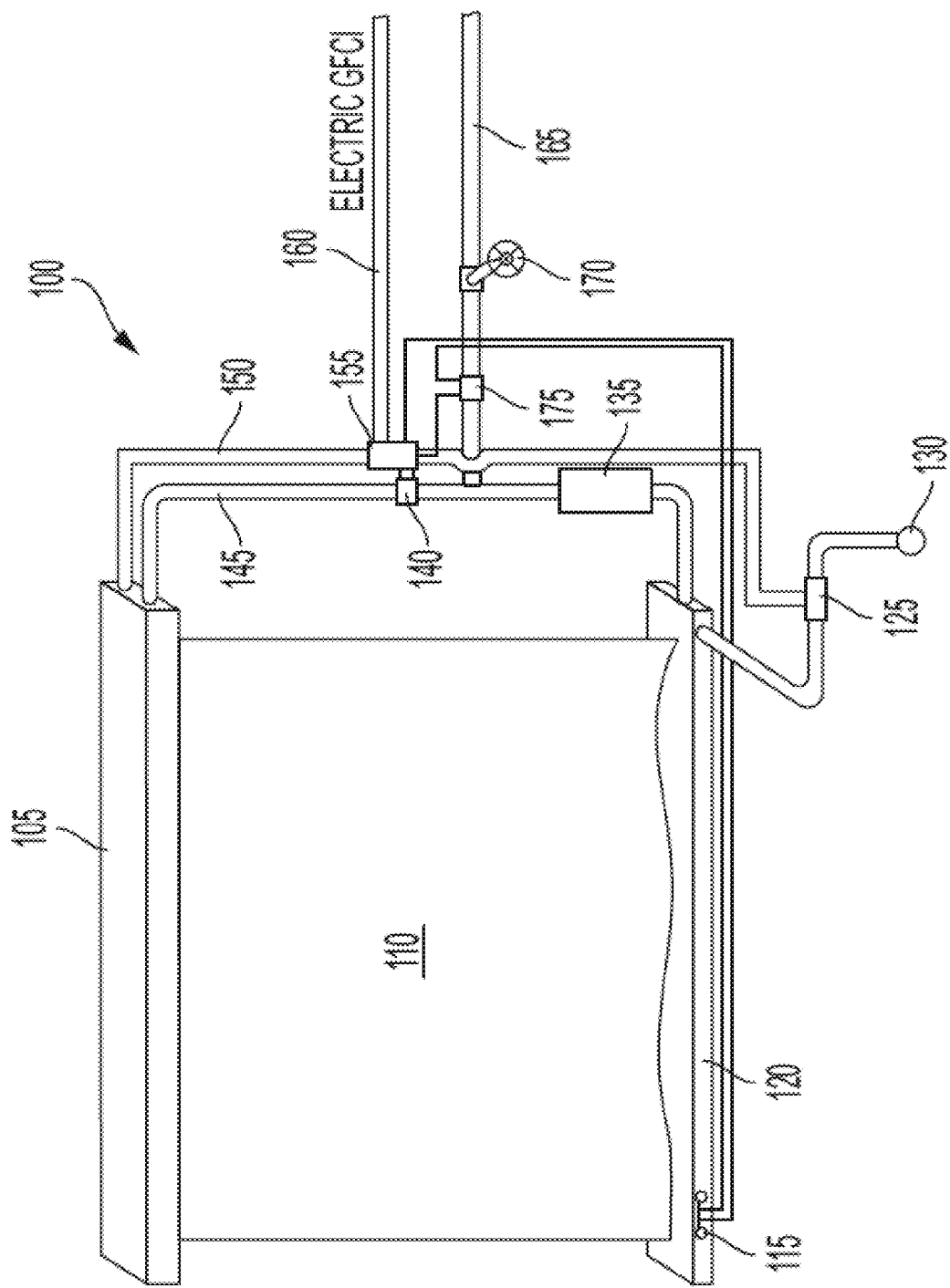
FIG. 6 is a diagrammatic representation of a water curtain apparatus according to an embodiment of the disclosure.

FIG. 6 is a diagrammatic representation of a water curtain apparatus according to an embodiment of the disclosure.

Aspects described in relation to FIG. 6 and/or illustrated in FIG. 6 may be utilized in any other embodiments herein. In particular, FIG. 6 illustrates a perspective side view of an embodiment of the system 1000. As shown in FIG. 6, an embodiment of the system 1000 in accordance with the present disclosure provides a water curtain or drape assembly 100 having a drape hood 105, a material drape 110, a float overflow shut-off 115, a collection return 120, a drainage line solenoid 125 which preferably is electric, a drainage line 130, an inline filter 135, a drape solenoid 140 which preferably is electric, a drape feed line 145, a pump (not shown), a pump power line 150, an on/off switch 155 to a power source 160 which preferably is a ground fault circuit interrupter (GFCI) power line for safety concerns, a feed line 165, and a shutoff valve 170.

The present embodiment of the system 1000, in one aspect, provides an indoor waterfall which utilizes a low viscosity liquid, such as water or other aqueous liquid, to form a continuous liquid film along a material drape 110 between two limiting elements the drape hood 105 and the collection return 120. The material drape 110 may be a photocatalyst or part of a bifunctional electrode. In certain embodiments, a second electrode which functions as a cathode is placed proximate to the material drape 110 and in electrical communication with the material drape 110 through the aqueous liquid. For example, the second electrode may be in the collection return 120, in the drape hood 105, or parallel to the material drape 110. In specific embodiments, the second electrode runs parallel to the material drape 110, as illustrated in FIG. 3. The second electrode may be spaced from the material drape 110 by about 0.1 to 10 cm, by about 1 to 10 cm, or by about 1 to 3 cm.

In some embodiments, the material drape 110 is the cathode and the second electrode is the photocatalyst.

The drape assembly 100 may be configured such that a light source illuminates the photocatalyst. When the light source illuminates the photocatalyst, the photocatalyst produces electron-hole pairs to generate OW radicals from the aqueous liquid. In certain embodiments, the light source is an LED.

The placement of the light source depends on the position of the photocatalyst. In some embodiments, the light source can be positioned in the drape hood 105 or the collection return 120, and configured to direct light toward the photocatalyst. Alternatively, the light source can be positioned in front of the material drape 110.

In certain embodiments where the material drape 110 is the photocatalyst and the second electrode runs parallel to the material drape, the second electrode can be configured as a mesh to allow light to penetrate through the second electrode to reach the photocatalyst.

FIG. 7A is a diagrammatic representation of a piston assembly according to an embodiment of the disclosure; and FIG. 7B is a cross-sectional view taken along the 3-3 in FIG. 7A.

Aspects described in relation to FIG. 7 and/or illustrated in FIG. 7 may be utilized in any other embodiments herein. In particular, FIG. 7A illustrates a first perspective side view of an embodiment of the system 1000 and FIG. 7B illustrates a second perspective side view of an embodiment of the system 1000. In particular, and embodiment of the system 1000 and associated method is illustrated in FIGS. 7A and 7B with reference to FIG. 6, wherein the material drape 110 is disposed within the drape hood 105 and suspended from the drape hood 105 towards the collection return 120. As water or other aqueous liquid is fed from feed line 165 to the drape feed line 145 into the drape hood 105, a pump 240 via intake 245 pumps the water or other aqueous liquid into a piston assembly 200 having a piston 203, a magnetic collar 205, a piston open position 210, a gutter 255, a gutter drain slit 215, a gutter groove 220, a piston closed position at a closed position 225, an elastic cord 230 attached to piston 203, a drape material track 235, gutter drain 250, and a piston sleeve 260.

The pumped liquid then pressurizes the piston sleeve 260 thereby causing the piston 203 to move longitudinally along the piston sleeve 260 from the closed position 225 to the piston open position 210. The magnetic collar 205 may in effect assist in pulling the piston 203 to the open position by using a reverse polarity implementation of the magnetic collar 205 to attract the piston 203. The elastic cord 230 assists in returning the piston 203 to the closed position 225 upon the reduction or removal of liquid pressure within the piston sleeve 260 accordingly. The gutter drain 250 may allow liquid located between the pump 240 and the piston 203 at the closed position 225 to be exhausted. The gutter drain slit 215 may allow liquid to flow from the piston sleeve 260 into the gutter 255 via the gutter groove 220 and into the drape material track 235. Once the liquid begins to fill the drape material track 235, liquid will accumulate and flow upon the material drape 110 disposed within the drape material track 235 in the direction of the collection return 120.

The water or other aqueous liquid may flow downward over the material drape 110 and through one side or both sides of the material drape 110, including a wicking effect for upward and downward flows while allowing ambient air to pass through. It should be noted that if a laminar flow of water or other aqueous liquid over the surfaces of the material drape 110 is created or controlled by the speed or velocity of pump 240, evaporation will occur, but the excess moisture while slightly restricting or controlling air movement will have the added benefit of "scrubbing" the air as it moves through the flowing water. This benefit may reduce pollutants, allergens, insects and the like. The gutter 255 may be filled manually without the use of pump 240 in some embodiments (not shown). The collection return 120 may either be independent or attached to a recirculation system as shown. The inline filter 135 may remove contaminants picked up during the movement of the water or other aqueous liquid.

An ionizing element (not shown) may be incorporated inline to create pH changes in the water or other aqueous liquid for sterilizing purposes.

Example 1

A BEEP embodiment of the disclosure was tested for combability in marine biological systems. To emulate a long-term acute toxicity test, a saltwater aquarium was maintained for one month using the reactor described herein. The test observed whether ammonia, nitrites and nitrate would stay within acceptable standard aquarium parameters and the fish would flourish. As the final oxidation product of ammonia, elevated nitrate levels were traditionally removed by dilution through water replacement. A standard photocatalytic prototype (See FIG. 8C) was employed for one week as a control prior to this test. The standard photocatalytic prototype was unable to efficiently process nitrites and nitrates from ammonia. The voltage supplied to the electrodes was maintained at 0.75 Volts and below detectable level in Milliamps.

Figure 8A:
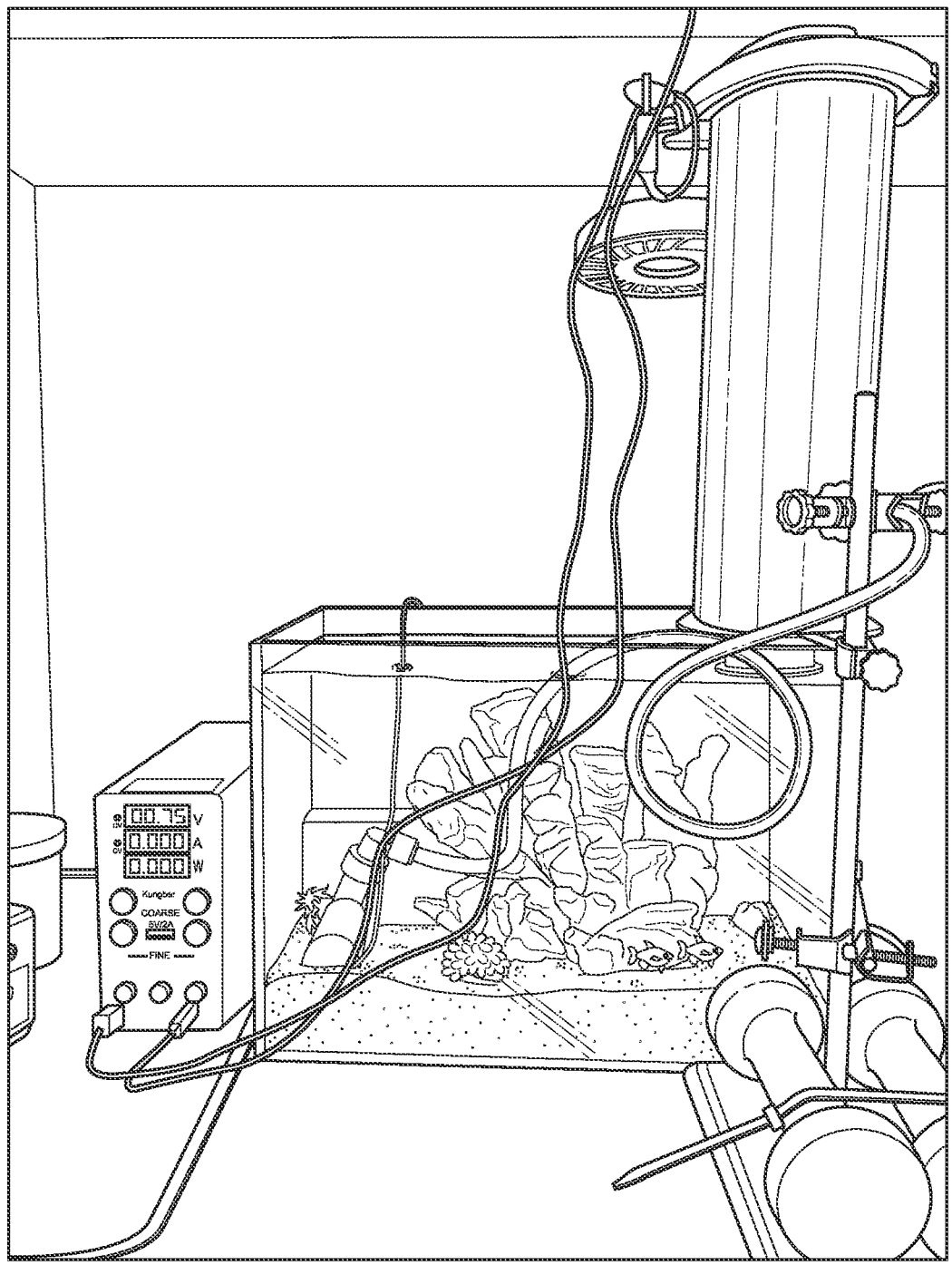
FIGS. 8A and 8B shows an image of a prototype and the internal set up of an embodiment of the disclosure.
Figure 8B:
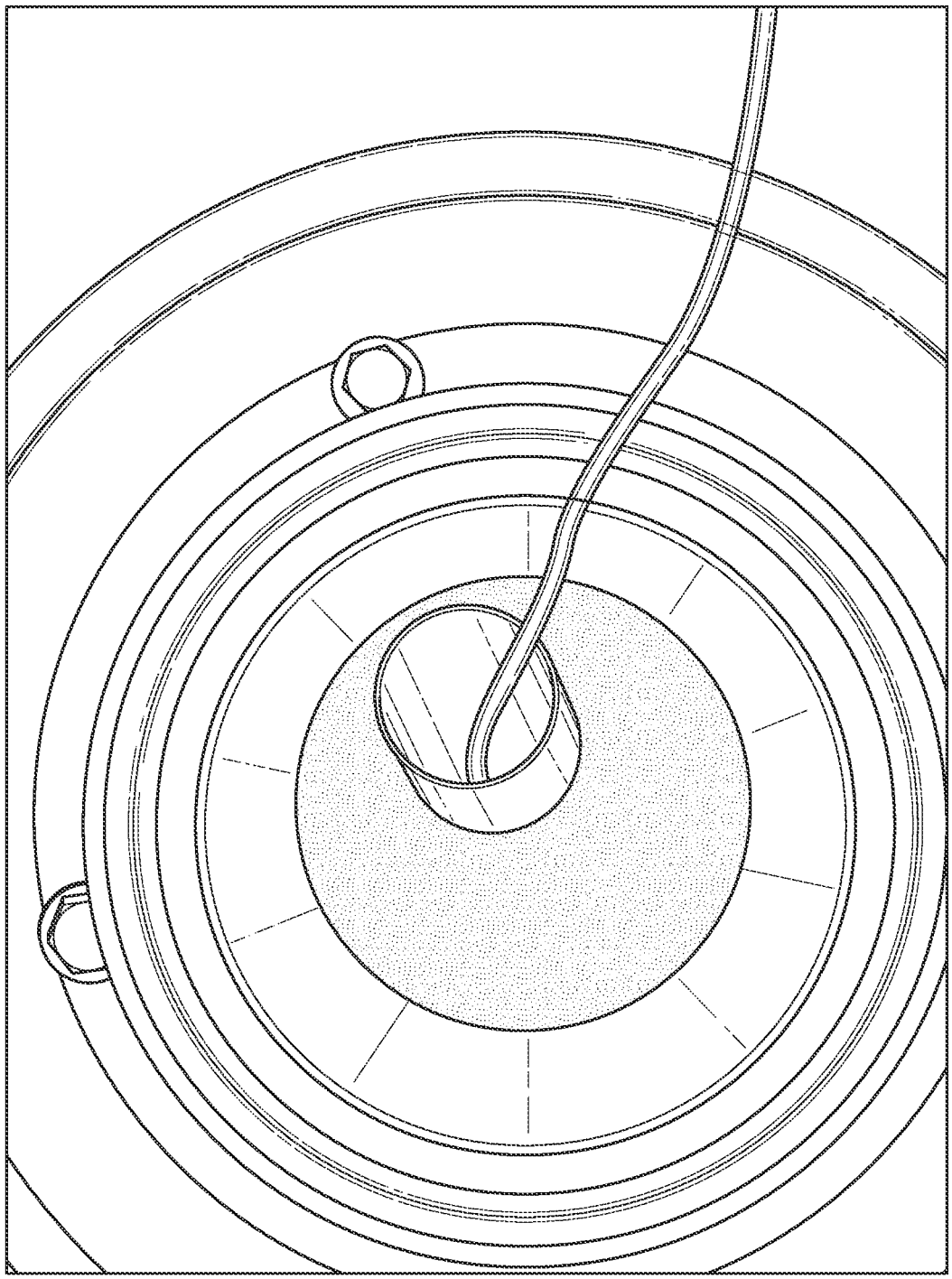
Figure 8C:
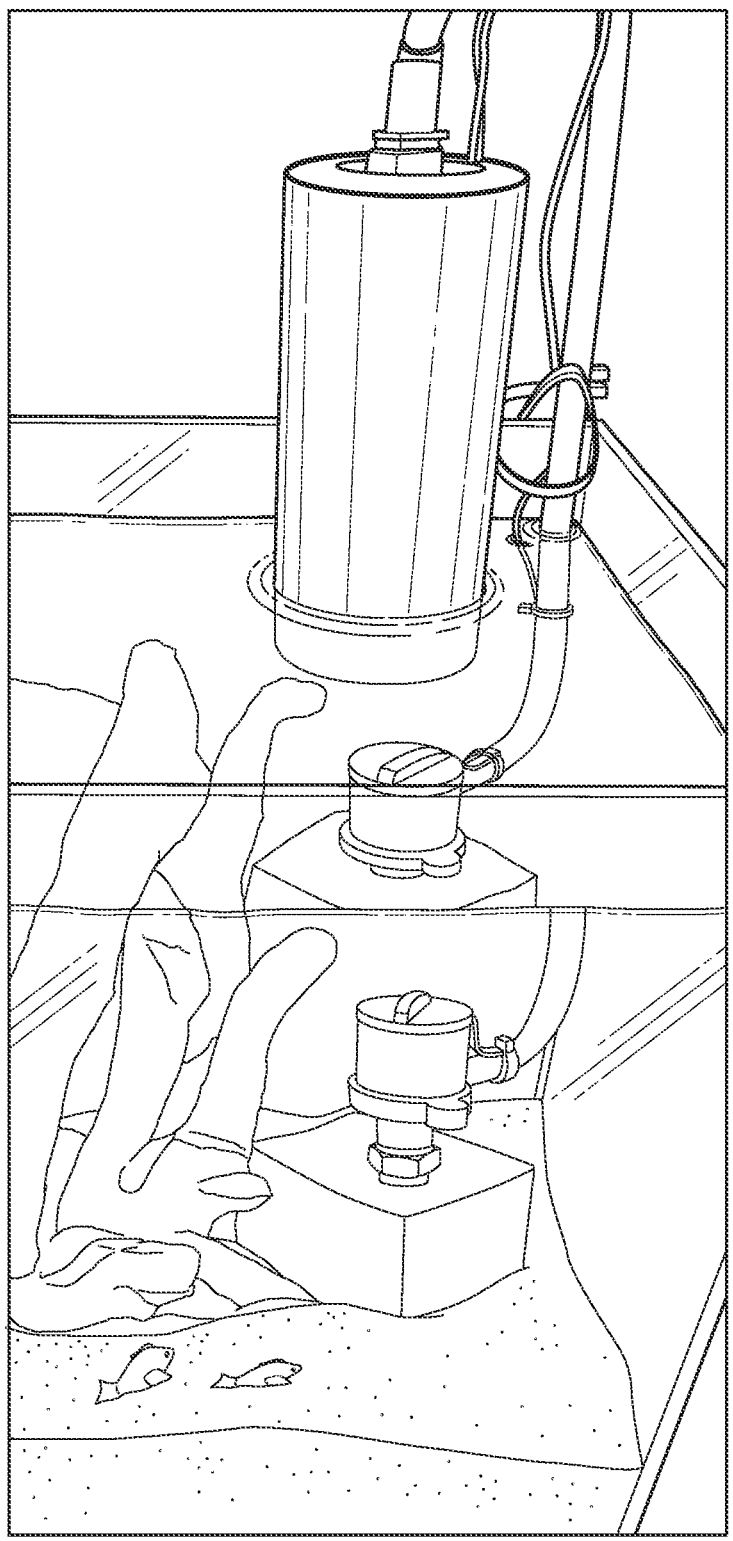
FIG. 8C is a non-BEEP prototype.
Figure 9A:
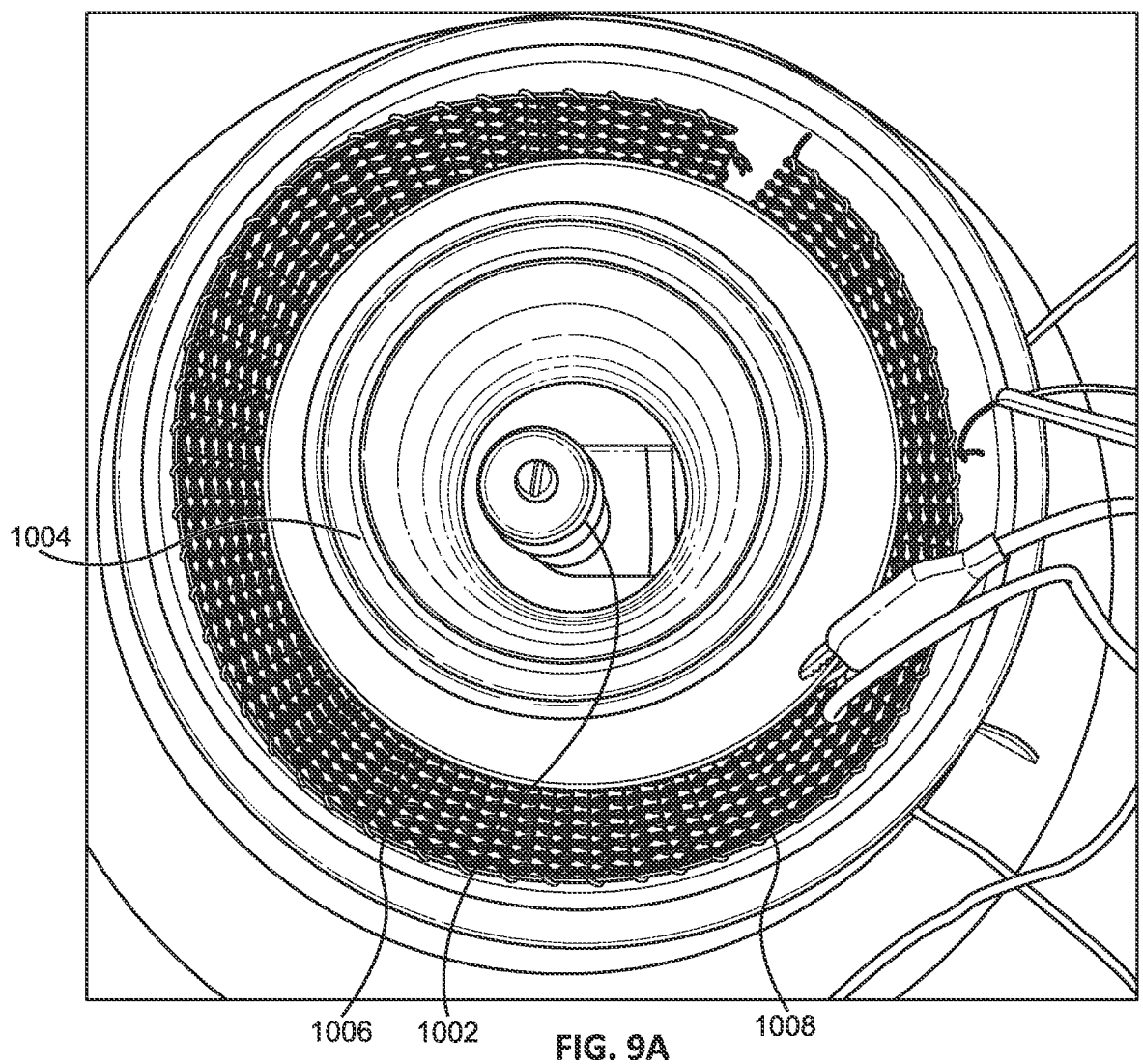
FIG. 9A and FIG. 9B show images of the internal set up of an embodiment of the disclosure, with and without UV assembly to display water presentation
Figure 9B:
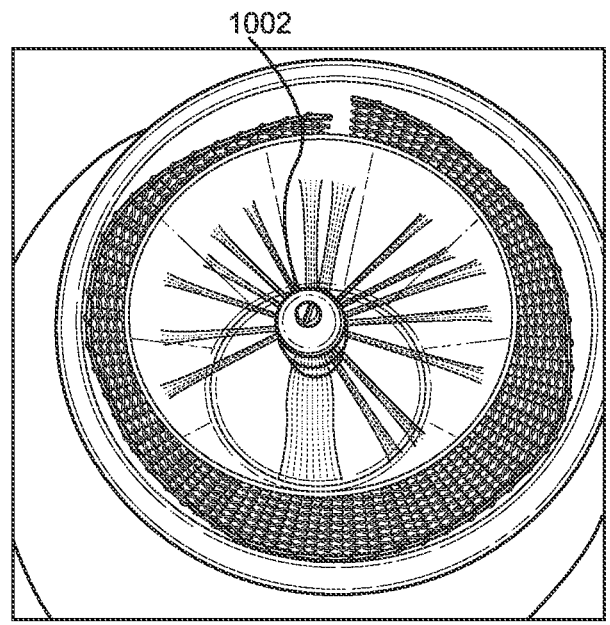

The BEEP photocatalytic reactor was made up of a titanium tube with the as-grown $TiO_2$ nanoporous material on the inner surface. This tube was held in place with a stainless-steel assembly which has a pump attached to a hose allowing it to fill the void between the photocatalytic anode and the stainless steel cathode. When running, the water overflows from the top of the photocatalyst and is exposed to the air as the water then runs down as a thin film on the $TiO_2$ nano-porous material inside the titanium tube. The UVA-LED assembly shown in FIG. 8B was secured in a glass tube suspended by its own wiring and when turned "on" it irradiated the inner surface of the titanium tube. In fact, because the electricity flowing through the ammonium fluoride/EG solution used to create the Nano-porous surface is placed central to the tube, the holes are optimally aligned for a centrally located light source to illuminate the structure. The water after the photo-oxidation process fell back into the aquarium/reservoir. FIGS. 8A and 8B shows an image of a prototype of the disclosure; and FIG. 9A and FIG. 9B show images of the internal set up of an embodiment of the disclosure. Measuring the effectiveness of a photocatalytic reactor normally requires a sacrificial dye, but an opportunity using off the shelf aquaria products to measure concentrations/changes of ammonia, nitrite and nitrate was employed. This provides an avenue for consumers to validate efficacy of a fresh or saltwater photocatalytic reactor.

Aspects described in relation to FIGS. 8 and 9 and/or illustrated in FIGS. 8 and 9 may be utilized in any other embodiments herein. In particular, an image of the system 1000 is provided in FIG. 8, with FIG. 9A showing an image of the internal view of the system 1000, and FIGS. 8B and 9B showing an image of the system 1000 in operation. In FIGS. 9A and 9B, a sprayer 1002 is centered with an LED assembly 1004 in between the sprayer 1002 and a radially disposed photocatalyst 1006, and a cathode 1008 further radially disposed around the photocatalyst 1006.

Example 2

The BEEP embodiment described in Example 1 was initially tested for efficacy by cleaning methylene blue with and without bias assistance. Methylene blue was selected as being representative of pharmaceutical drugs as methylene blue is a salt used as a medication and dye. As a medication, methylene blue is mainly used to treat methemoglobinemia. Furthermore, the amount of methylene blue in solution can be readily measured by absorbance.

Figure 10:
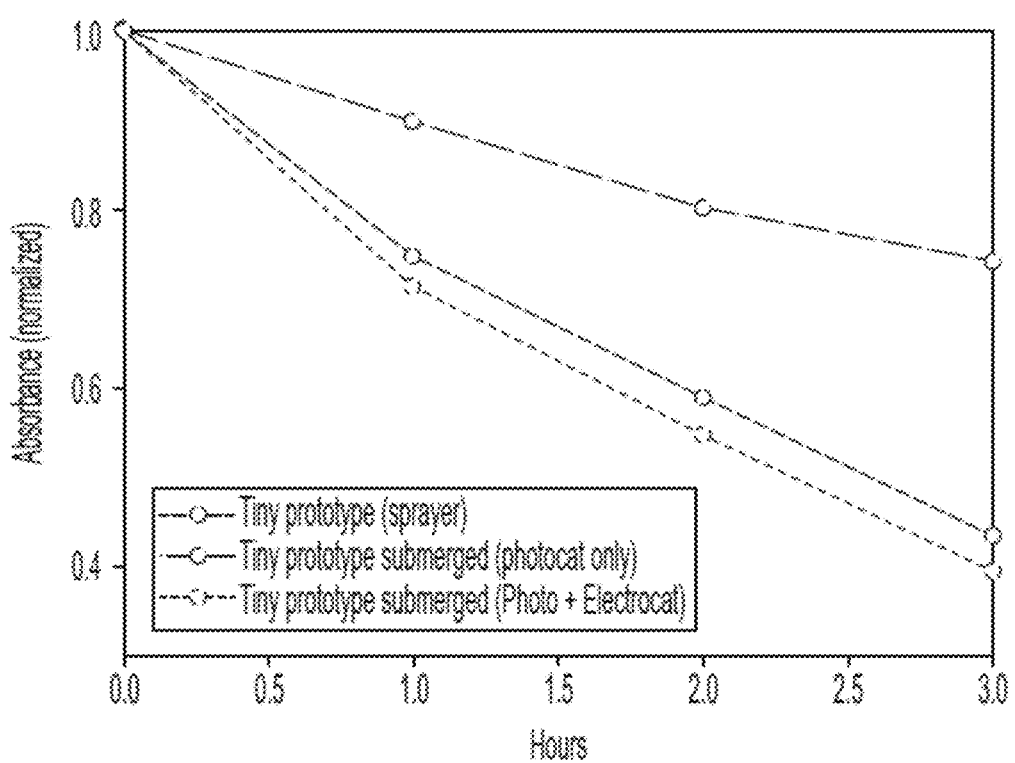
FIG. 10 shows the results of cleaning from an embodiment of the disclosure.

The "tiny" prototype was submerged about 70% in water (10,000 ppm salt and 20 mg methylene blue in 6 L water). A constant 500 mA current was applied between the inner stainless-steel cathode and outer $TiO_2$ anode. One test was performed with only the photocatalyst, and one test was performed with both the photocatalyst and electro cathode. The submerged data was compared with photocatalysis data performed with a sprayer running the water and spraying on the mesoporous titanium tubes. The results are illustrated in FIG. 10.

During the experiment, the amount of methylene blue in solution was measured by absorbance. As illustrated by the data in FIG. 10, activation of both the photocatalyst and electrocatalyst resulted in superior removal of the methylene blue as compared to the electrocatalyst alone.

Figure 11:
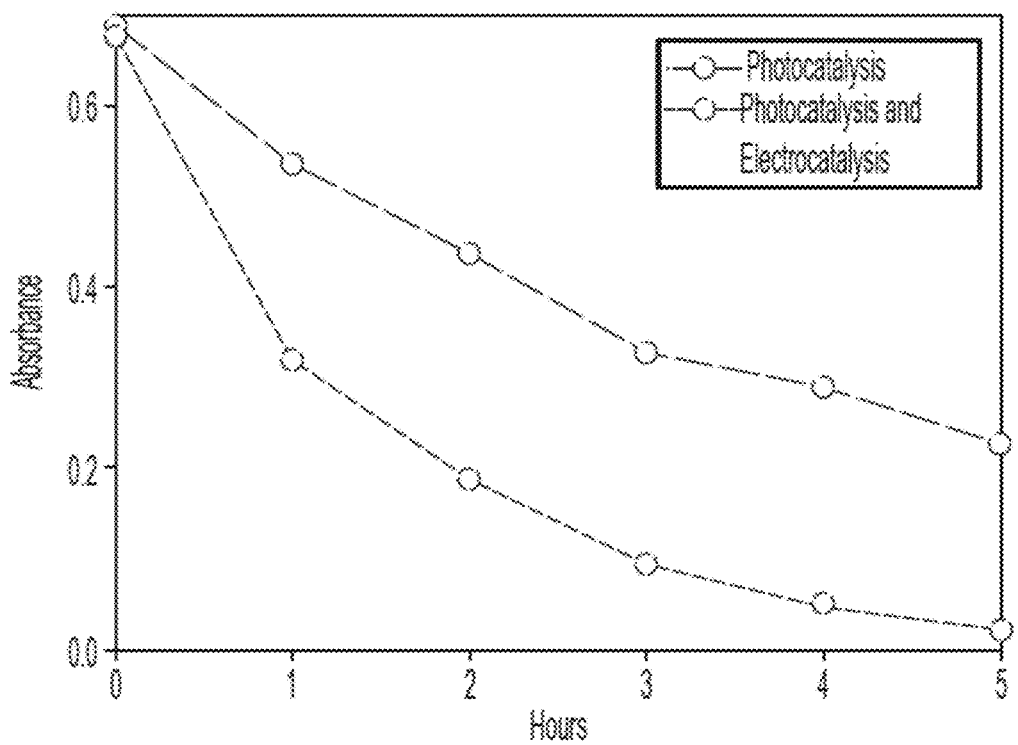
FIG. 11 shows the results of cleaning from an embodiment of the disclosure.

FIG. 11 provides the results of a variation of the above experiment using the prototype of FIGS. 9, where 4000 ppm NaCl solution was used and current was kept at a constant 200 mA.

Figure 12:
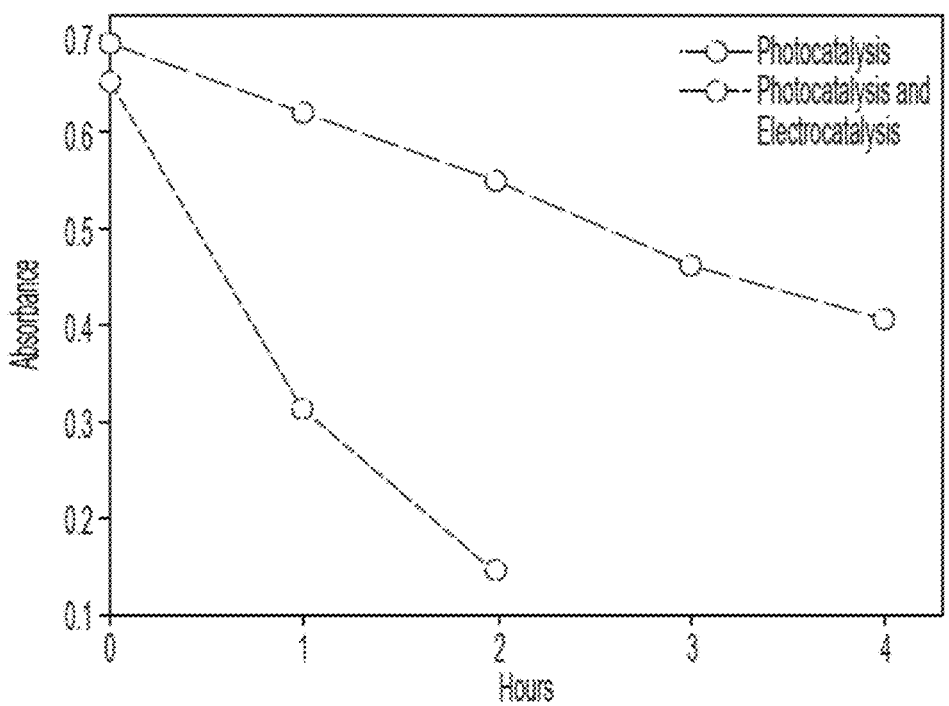
FIG. 12 shows the results of cleaning from an embodiment of the disclosure.

FIG. 12 provides the results of a variation of the above experiment using the prototype of FIG. 9 where 2000 ppm NaCl solution was used and current was kept at a constant 200 mA.

Example 3

A two-month-long experiment was conducted on a heavily used hot tub with a water volume of 1200 L using a non-BEEP embodiment, which can be converted with the addition of a cathode based on embodiments of the above disclosure. Before the testing period, the hot tub was completely drained and cleaned to rid the presence of all chemicals. During two months of testing, no other means of sanitization were used (e.g., salt, ozone, liquid chlorine, bromine, or electrolytic systems which converts added salt into free chlorine). In the two-month test, 60 bodies (around 10 different users) went in the hot tub and the average usage time per user was between 30 to 40 min.

Figure 13A:
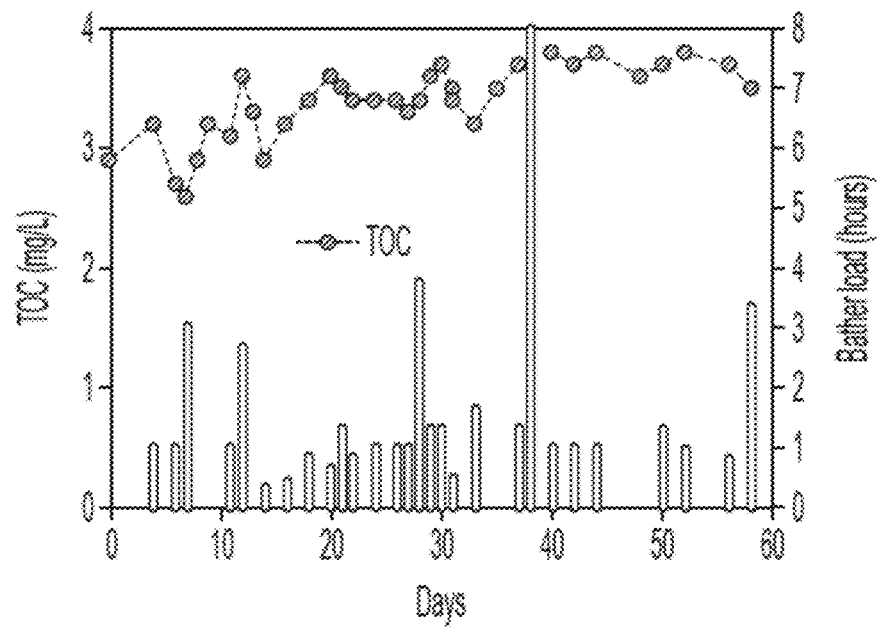
FIG. 13A shows the results of cleaning from a non-BEEP prototype of the disclosure.
Figure 13B:
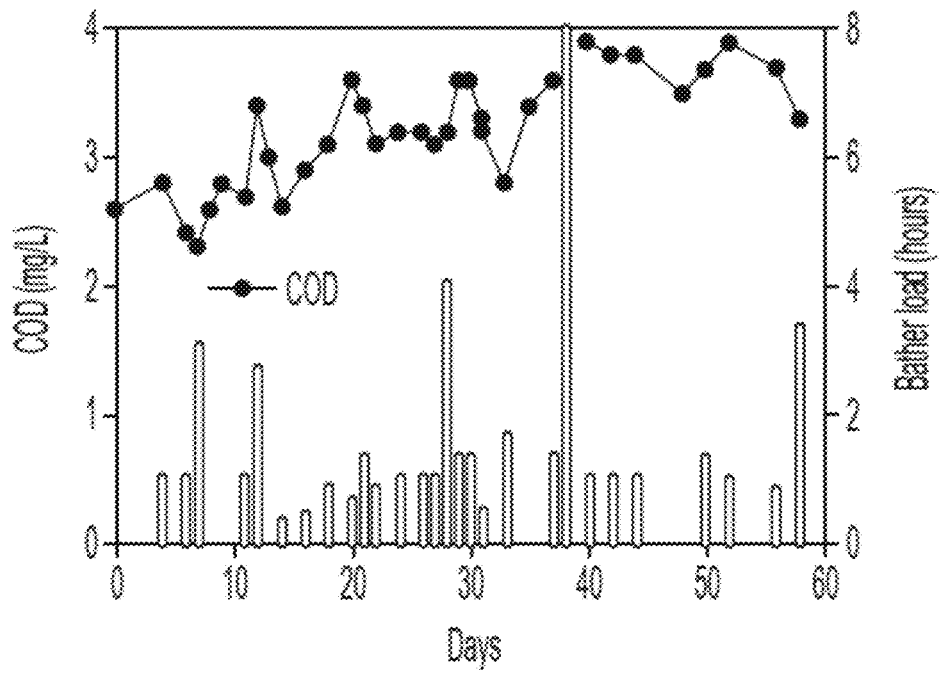
FIG. 13B shows the results of cleaning from a non-BEEP prototype of the disclosure.
Figure 13C:
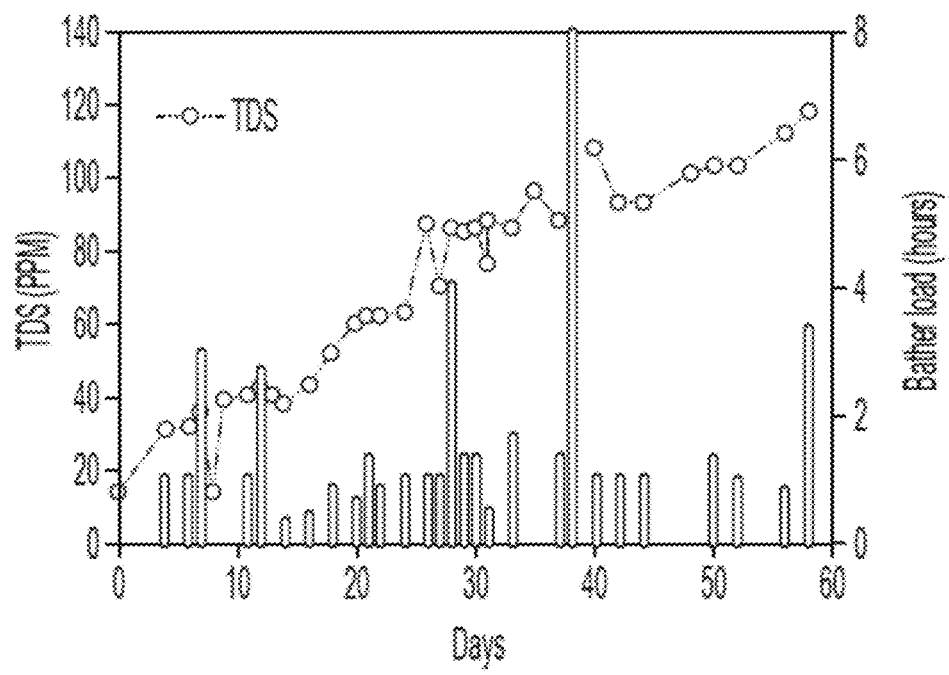
FIG. 13C shows the total dissolved solids based on testing data from a non-BEEP prototype of the disclosure.

FIGS. 13A-C shows the plotted data collected during the test run. FIG. 13A is TOC (Total Organic Carbon) which is a measure of the total amount of carbon in organic compounds in pure water and aqueous systems. The initial tap water TOC was 2.7 ppm and after two months of heavy use and big bather loads, the TOC remained very stable at close to 3.2 ppm. This shows that the photocatalytic reactor was able to oxidize most of the organic compounds entering the water.

When not maintained and cleaned properly, hot tubs provide an ideal environment for bacteria and viruses to grow, causing skin, eye, and ear infections, as well as other serious diseases. In the study, COD (Chemical Oxygen Demand) was regularly measured which was used as a general indicator of water quality (FIG. 13B). Biochemical Oxygen Demand (BOD) was estimated from COD measurements and represents the amount of oxygen consumed by bacteria and other microorganisms while they decompose organic matter under aerobic (oxygen is present) conditions at a specified temperature. In general, a higher COD or BOD value means the water has bacterial growth in it.

In our testing, no significant increase in the COD value was observed even with a very high bather load showing that the photocatalytic reactor was able to keep the bacterial growth under control. Without wishing to be bound to theory, the photoreactor oxidizes organic materials eliminating the nutrient media for the bacteria. The photoreactor also directly oxidizes already present or introduced pathogens through photocatalytic oxidation. It was, however, noticed that a constant increase in the Total Dissolved Solids (TDS) value represents the total concentration of dissolved substances in water (FIG. 13C). Common inorganic salts that can be found in water include calcium, magnesium, potassium, and sodium, which are all cations, and carbonates, nitrates, bicarbonates, chlorides, and sulfates. The initial water has TDS value of 20 mg/L and the hot tub water after two months of usage and photocatalytic treatment has a value of around 120 mg/L. This increase is most likely due to the addition of different cations and anions present in the human sweat. The value is still safe as according to EPA USA up to 500 mg/L is good for drinking.

Example 4

Figure 14:
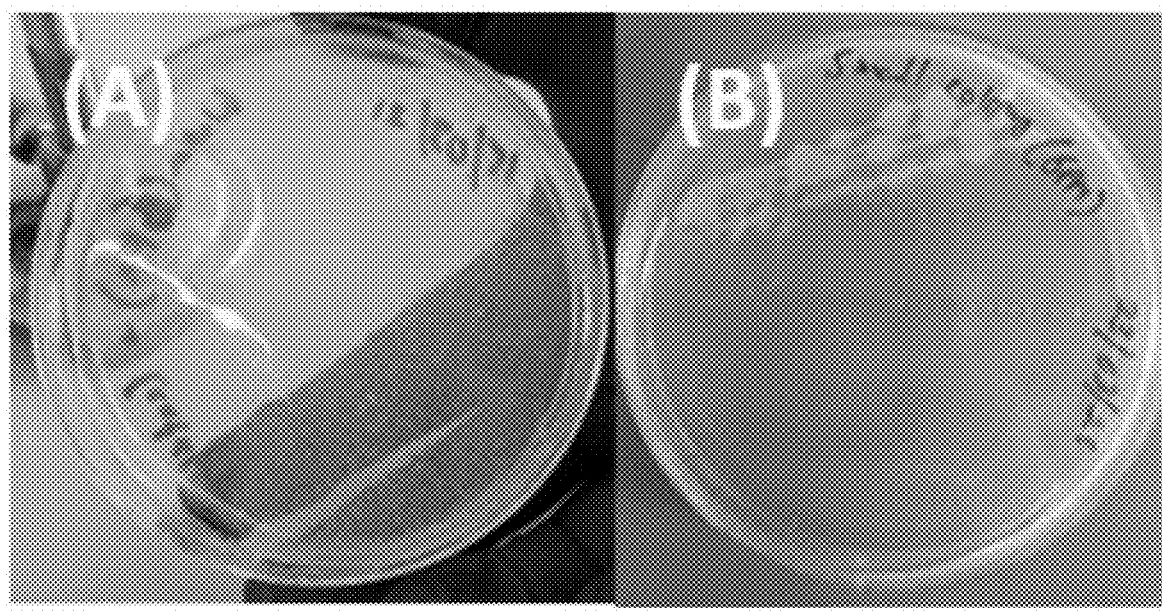
FIG. 14 provides three panels, panels (A) and (B) showing plating and incubation of samples, and panel (C) showing FLAT analysis from a non-BEEP prototype.
Figure 14:
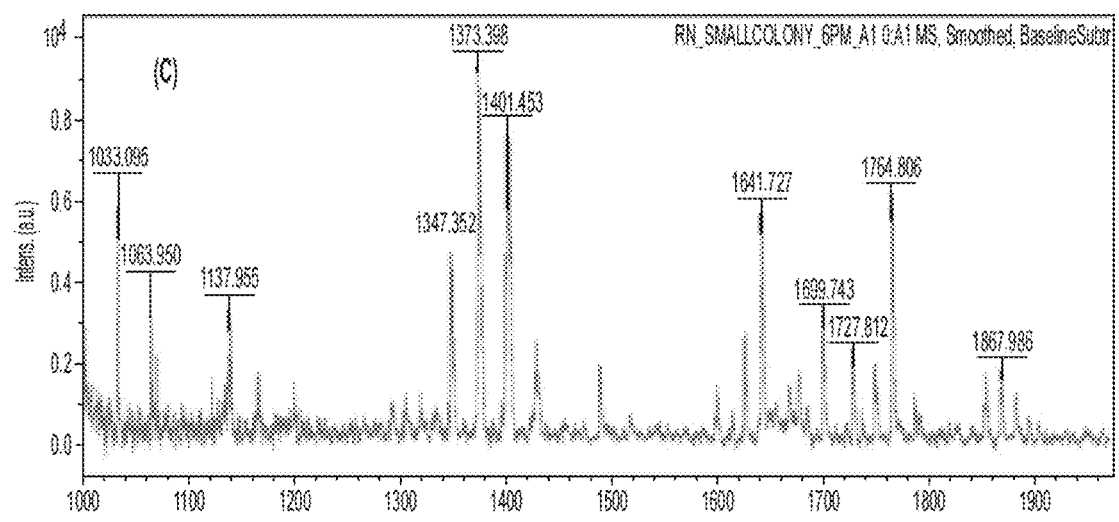

Bacterial studies were performed on treated hot tub water to ensure user safety using a non-BEEP embodiment, which can be converted with the addition of a cathode based on embodiments of the above disclosure. Hot tub water (20 ml) was collected in falcon tubes and centrifuged at for 15 minutes. The supernatant was discarded, and the pellet were suspended in 500 µL of LB. 10 µL of the resuspension was spread plated on LB agar and incubated. Bacteria were identified using FLAT (FIG. 14, section (C)). One µL of citric acid buffer was added to each well on a MALDI plate. Colonies were picked from the LB agar plate and resuspended in buffer. The plate was incubated at 110° C. for 30 minutes, then washed with sterile deionized water. FLAT analysis revealed very little bacterial growth in hot tub water, even after two months of heavy use. The slight growth on the plate shown in FIG. 14, section (A)-(B), could not result in any FLAT analysis database match. This indicates that it is a reminiscent byproduct of the oxidation products of P. Aeruginosa bacteria.

The above results revealed that even after two months of constant heavy usage, the hot tub water was very clean and almost no bacterial growth was observed.

Figure 15:
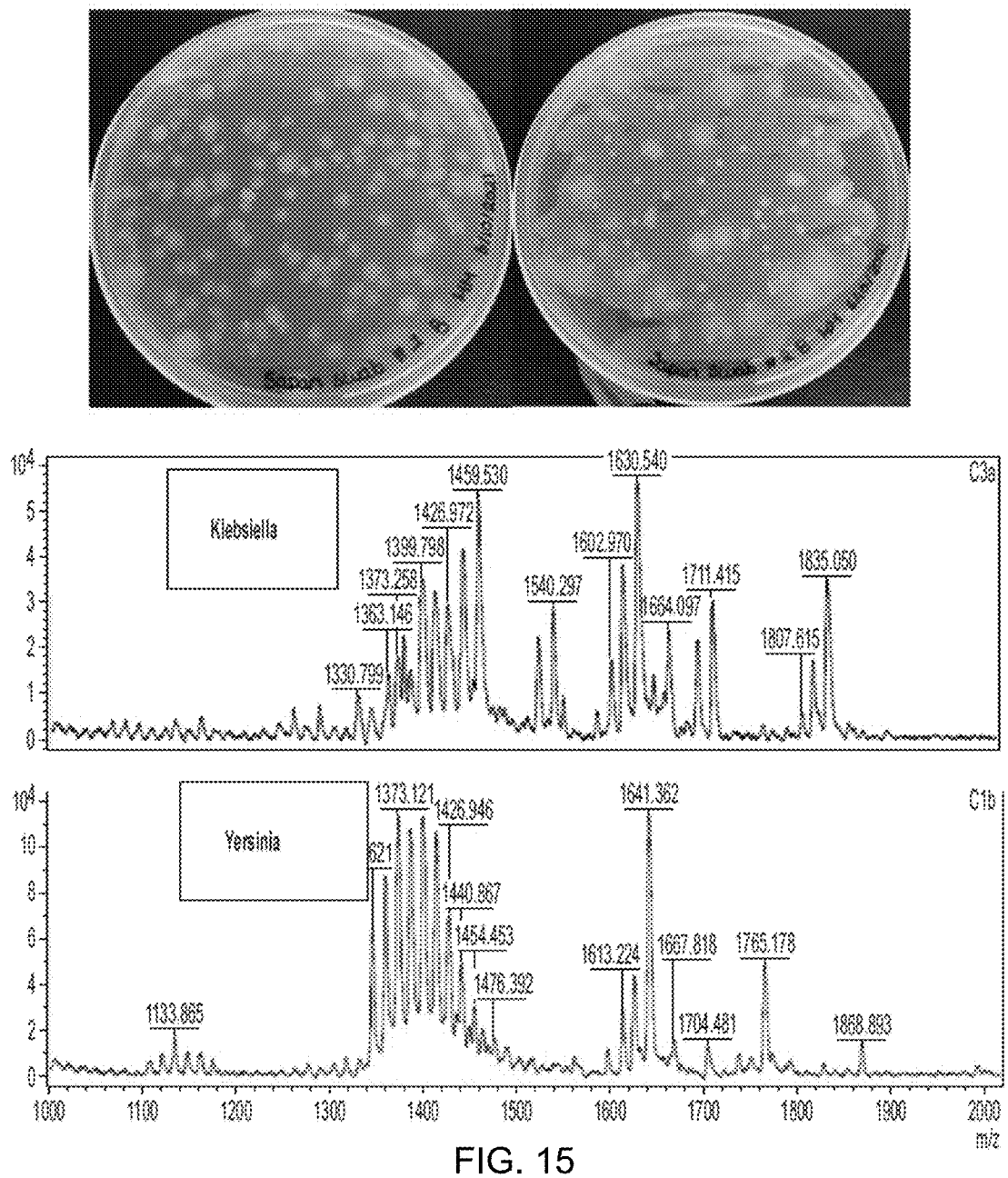
FIG. 15 provides four panels, the top two panels showing plating and incubation of samples, and the bottom two panels showing characterization of bacteria from a non-BEEP prototype.

As a control experiment, another long-term experiment was performed where no sanitization was used to see how long the water of the hot tub stay usable. However, after a couple of weeks, the TOC and COD values started to go above 4 and after a month of usage, the water sample from the hot tub showed very vibrant bacterial growth which can be seen in FIG. 15.

Both these bacteria, *Klebsiella* and *Yersinia* can cause illness in humans. These results show that how important is the role of sanitization in hot tubs.

Example 5

An independent bacterial disinfection study was performed using *Escherichia coli* DH5a using a non-BEEP embodiment, which can be converted with the addition of a cathode based on embodiments of the above disclosure. 1.5 L of *E. coli* DH5a bacterial suspension was prepared from single colony inoculation. A single colony of *E. coli* was spiked into 5 mL LB broth (BD Difco) and incubated at 37° C. for 16 hours with continuous shaking at 180 rpm. The *E. coli* culture was added to 145 mL of LB broth and incubated a further 16 h under the same conditions. Absorbance after the second incubation was 0.282. The culture was centrifuged, and the supernatant discarded, and the pellet was resuspended in 2 L sterile deionized water.

Figure 16:
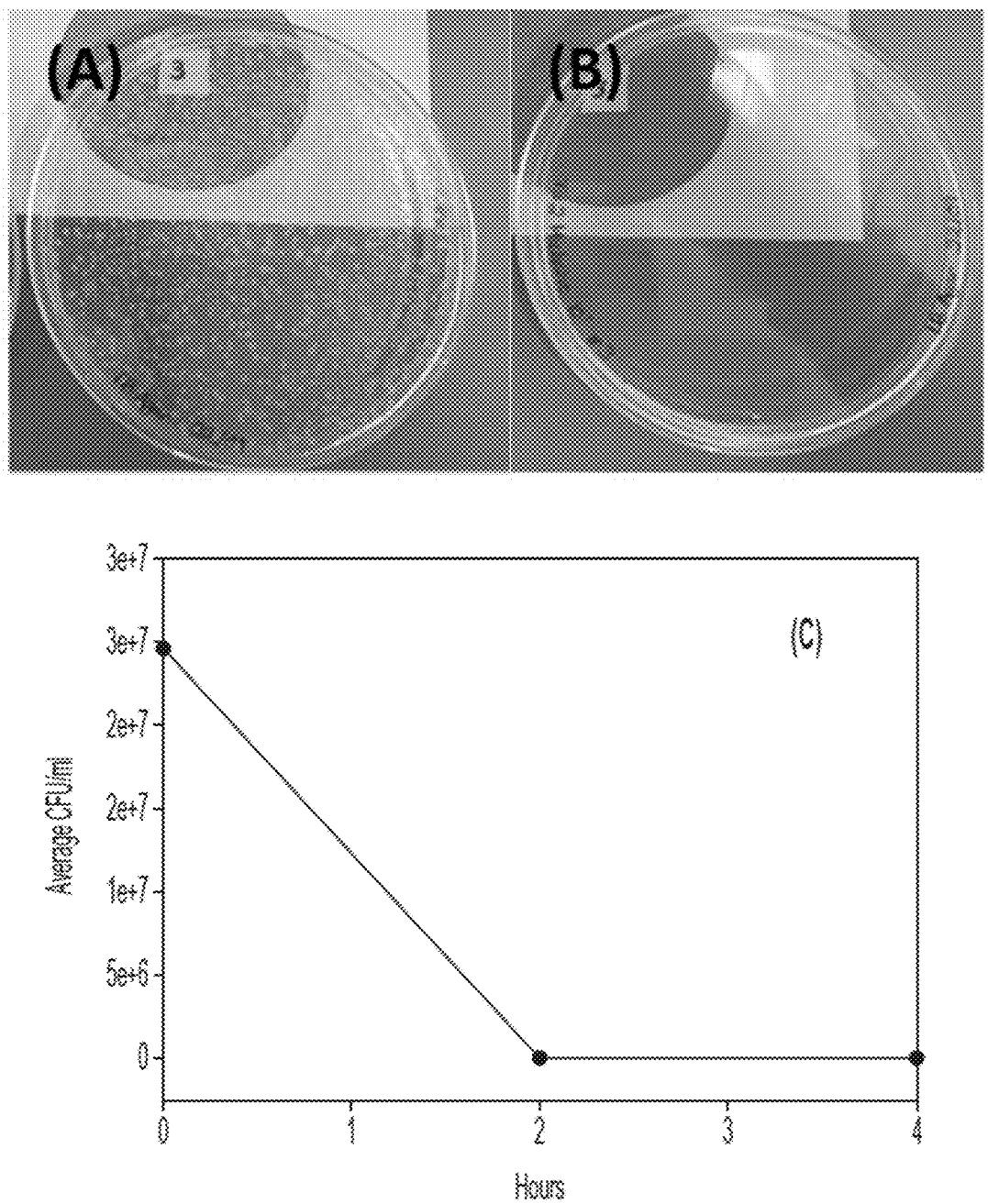
FIG. 16 provides three panels, panels (A) and (B) showing plating and incubation of samples, and panel (C) showing average CFU/ml over time from a non-BEEP prototype.

As a control, 40 mL aliquot of suspension was collected prior to filling the machine. The reactor was filled with suspension and turned on. The sample line was flushed and a 5 mL sample was collected at 0 hours, 2 hours, and 4 hours. A 1 mL aliquot of each sample and the control were serially diluted to 10-6 at each time point. 100 μL of undiluted, 10-4, and 10-6 were spread plated in triplicate on LB agar (BD Difco, Fisher Bioreagents) and incubated for 24 h at 37° C. Following incubation, CFU/mL was determined. After two hours of water treatment no colonies were visible (FIG. 16, section (B)). CFU/mL of the control remained constant over 4 hours. This shows the efficacy of the embodiment towards the disinfection of the water. This technology can be employed in remote areas where there is a shortage of clean drinking water. FIG. 16 shows the results from the bacterial study. FIG. 16, section (A), shows the numerous CFU present in the initial sample and FIG. 16, section (B), shows the plate with no CFU just after two hours of the photooxidation. FIG. 16, section (C), shows the average CFU/ml per hr.

Example 6

A BEEP embodiment of the disclosure was tested for the ability to degrade perfluoroalkyl substances (PFAS). The embodiment was consistent with FIG. 2 of the disclosure, where the resident electrolyte was salt water with approximately 35 g/L of salt. In the tests, a sample of water was prepared by Weck Labs with various PFAS. After running the sample(s) through the embodiment, samples were returned to Weck Labs to determine a change in the concentration of PFAS in two tests: 537.1 and 537M. The results are provided in the below Table:

| IUPAC Name | 537.1 Test | Doping levels 537.1 | 537M Test | Doping Levels 537M |
|---|---|---|---|---|
| 2-(8-chloro-1,1,2,2,3,3,4,4,5,5,6,6,7,7,8,8-hexadecafluorooctoxy)-1,1,2,2-tetrafluoroethanesulfonate | ND | 20.5 | 3.3 | 38 |
| 2-(6-chloro-1,1,2,2,3,3,4,4,5,5,6,6-dodecafluorohexoxy)-1,1,2,2-tetrafluoroethanesulfonate | ND | 20.9 | 16 | 41 |
| 2,2,3-Trifluoro-3-[1,1,2,2,3,3-hexafluoro-3-(trifluoromethoxy)propoxy]propanoic acid | 26 | 21.3 | 31 | 25 |
| 2,3,3,3-Tetrafluoro-2-(heptafluoropropoxy)propanoic acid | 33 | 21.9 | 36 | 36 |
| Heptafluorobutanoic acid | | | 37 | 35 |
| Nonafluoropentanoic acid | | | 36 | 35 |
| Undecafluorohexanoic acid | 31 | 21.6 | 36 | 35 |
| Tridecafluoroheptanoic acid | 29 | 21.2 | 37 | 35 |
| Pentadecafluorooctanoic acid | 28 | 21.7 | 59 | 35 |
| Heptadecafluorononanoic acid | 15 | 21.7 | 26 | 35 |
| Nonadecafluorodecanoic acid | ND | 21.6 | 15 | 34 |
| Henicosafluoroundecanoic acid | ND | 21.3 | 5.1 | 35 |
| Tricosafluorododecanoic acid | ND | 20.9 | 1.7 | 38 |
| Pentacosafluorotridecanoic acid | ND | 20.9 | 0.89 | 36 |
| Heptacosafluorotetradecanoic acid | ND | 20.9 | ND | 34 |
| Hentriacontafluorohexadecanoic acid | | | ND | 32 |
| Pentatriacontafluorooctadecanoic acid | | | ND | 45 |
| Nonafluorobutane-1-sulfonic acid | 32 | 22.5 | 34 | 36 |
| Perfluoropentane sulfonoic acid | | | 31 | 33 |
| Tridecafluorohexane-1-sulfonic acid | 26 | 22.6 | 30 | 33 |
| Pentadecafluoroheptane-1-sulfonic acid | | | 28 | 42 |
| Heptadecafluorooctane-1-sulfonic acid | 13 | 21.9 | 21 | 34 |
| 1,1,2,2,3,3,4,4,5,5,6,6,7,7,8,8,9,9,9-nonadecafluorononane-1-sulfonic acid | | | 10 | 40 |
| Henicosafluorodecane-1-sulfonic acid | | | 3.6 | 37 |
| 4,4,5,5,6,6,6-heptafluorohexanoic acid | | | 34 | 49 |
| 4,4,5,5,6,6,7,7,8,8,8-Undecafluorooctanoic acid | | | 12 | 12 |
| 4,4,5,5,6,6,7,7,8,8,9,9,10,10,10-Pentadecafluorodecanoic acid | | | ND | 6.8 |
| 3,3,4,4,5,5,6,6,6-Nonafluoro-1-hexanesulfonic acid | | | 30 | 29 |
| 3,3,4,4,5,5,6,6,7,7,8,8,8-Tridecafluorooctane-1-sulfonic acid | | | 29 | 35 |
| 3,3,4,4,5,5,6,6,7,7,8,8,9,9,10,10,10-Heptadecafluorodecane-1-sulfonic acid | | | 16 | 34 |
| 3,3,4,4,5,5,6,6,7,7,8,8,9,9,10,10,11,11,12,12,12-henicosafluorododecane-1-sulfonic acid | | | 2.4 | 34 |

-continued

| IUPAC Name | 537.1 Test | Doping levels 537.1 | 537M Test | Doping Levels 537M |
|---|---|---|---|---|
| N-Ethyl-1,1,2,2,3,3,4,4,5,5,6,6,7,7,8,8,8-heptadecafluoro-N-(2-hydroxyethyl)octane-1-sulfonamide | | | ND | 55 |
| N-Ethyl-1,1,2,2,3,3,4,4,5,5,6,6,7,7,8,8,8-heptadecafluorooctane-1-sulfonamide | ND | 20.8 | ND | 35 |
| N-Ethyl-N-(1,1,2,2,3,3,4,4,5,5,6,6,7,7,8,8,8-heptadecafluorooctane-1-sulfonyl)glycine | | | ND | 34 |
| 1,1,2,2,3,3,4,4,5,5,6,6,7,7,8,8,8-Heptadecafluoro-N-(2-hydroxyethyl)-N-methyloctane-1-sulfonamide | | | ND | 56 |
| 1,1,2,2,3,3,4,4,5,5,6,6,7,7,8,8,8-Heptadecafluoro-N-methyloctane-1-sulfonamide | ND | 20.6 | ND | 45 |
| N-(1,1,2,2,3,3,4,4,5,5,6,6,7,7,8,8,8-Heptadecafluorooctane-1-sulfonyl)-N-methylglycine | | | ND | 37 |
| 1,1,2,2,3,3,4,4,5,5,6,6,7,7,8,8,8-Heptadecafluorooctane-1-sulfonamide | | | ND | 34 |

As illustrated by the above results, PFAS were reduced, in some cases—below detectable levels.

The many features and advantages of the disclosure are apparent from the detailed specification, and thus, it is intended by the appended claims to cover all such features and advantages of the disclosure which fall within the true spirit and scope of the disclosure. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

What is claimed is:

1. A system, comprising:
    a light source configured to emit light at a wavelength;
    a cathode disposed radially around or parallel to the light source;
    a photocatalyst anode disposed radially around or parallel to the cathode and configured to be illuminated by the light source, and presenting a photocatalytic surface to the light emitted by the light source;
    a power source electronically connected to the photocatalyst anode and the cathode and configured to apply a positive charge to the photocatalyst anode and a negative charge to the cathode creating a bias between the cathode and the photocatalyst anode; and
    the photocatalyst anode and the cathode being configured to have a fluid therebetween, wherein the fluid contains one or more pollutants which are degraded when the photocatalyst anode is illuminated,
    wherein the light source illuminates the photocatalyst anode to excite electron-hole pairs in the photocatalyst anode; and
    wherein the cathode allows light to penetrate and excite the photocatalyst anode.

2. The system of claim 1, wherein the light source comprises a light emitting diode (LED).

3. The system of claim 2, wherein the fluid comprises seawater.

4. The system of claim 3, wherein the photocatalyst anode comprises $TiO_2$.

5. The system of claim 4, wherein the photocatalyst anode is perforated.

6. The system of claim 4, wherein the cathode is perforated and is light permeable and comprises stainless steel.

* * * * *